United States Patent
Gobbi et al.

(10) Patent No.: US 12,071,420 B2
(45) Date of Patent: Aug. 27, 2024

(54) PYRIDINE AND PYRAZINE COMPOUNDS AS INHIBITORS OF CANNABINOID RECEPTOR 2

(71) Applicants: HOFFMANN-LA ROCHE INC., Little Falls, NJ (US); ETH ZUERICH, Zurich (CH)

(72) Inventors: Luca Gobbi, Basel (CH); Uwe Grether, Basel (CH); Julian Kretz, Basel (CH); Simon M. Ametamey, Zurich (CH)

(73) Assignees: HOFFMANN-LA ROCHE INC., Little Falls, NJ (US); ETH ZUERICH, Zurich (CH)

( * ) Notice: Subject to any disclaimer, the term of this patent is extended or adjusted under 35 U.S.C. 154(b) by 710 days.

(21) Appl. No.: 17/125,650

(22) Filed: Dec. 17, 2020

(65) Prior Publication Data

US 2021/0115011 A1  Apr. 22, 2021

Related U.S. Application Data

(63) Continuation of application No. PCT/EP2019/066811, filed on Jun. 25, 2019.

(30) Foreign Application Priority Data

Jun. 27, 2018  (EP) ..................... 18180137

(51) Int. Cl.
 *C07D 401/04*  (2006.01)

(52) U.S. Cl.
 CPC .................. *C07D 401/04* (2013.01)

(58) Field of Classification Search
 CPC .................. C07D 401/04
 See application file for complete search history.

(56) References Cited

U.S. PATENT DOCUMENTS

| | | | |
|---|---|---|---|
| 9,303,012 B2 | 4/2016 | Bendels et al. | |
| 9,321,727 B2 | 4/2016 | Bissantz et al. | |
| 9,403,808 B2 | 8/2016 | Bissantz et al. | |
| 9,409,866 B2 | 8/2016 | Grether et al. | |
| 9,512,141 B2 | 12/2016 | Dhurwasulu et al. | |
| 9,522,886 B2 | 12/2016 | Frei et al. | |
| 10,155,942 B2 | 12/2018 | Kurihara et al. | |
| 10,308,659 B2 | 6/2019 | Gavelle et al. | |
| 10,912,849 B2 | 2/2021 | Wu et al. | |
| 11,479,807 B2 | 10/2022 | Kennedy et al. | |
| 2005/0245544 A1 | 11/2005 | Bell et al. | |
| 2007/0105861 A1 | 5/2007 | Lee et al. | |
| 2008/0280868 A1 | 11/2008 | Eatherton et al. | |
| 2020/0182940 A1 | 6/2020 | Tsai | |
| 2020/0239490 A1 | 7/2020 | Frei et al. | |
| 2021/0115012 A1 | 4/2021 | Ametamey et al. | |
| 2021/0115027 A1 | 4/2021 | Ametamey et al. | |
| 2021/0130334 A1 | 5/2021 | Ametamey et al. | |

FOREIGN PATENT DOCUMENTS

| | | |
|---|---|---|
| CL | 2020002927 A1 | 3/2021 |
| CN | 1703402 A | 11/2005 |
| CN | 101522644 A | 9/2009 |
| CN | 103608332 A | 2/2014 |
| CN | 104024232 A | 9/2014 |
| CN | 104837830 A | 8/2015 |
| CN | 104854092 A | 8/2015 |
| CN | 106132958 A | 11/2016 |
| CN | 106349156 A | 1/2017 |
| CN | 106458984 A | 2/2017 |
| CO | 6890101 A2 | 3/2014 |
| CO | 2017005374 A | 8/2017 |
| ES | 2388833 T3 | 10/2012 |
| JP | 2014516071 A | 7/2014 |
| JP | 2014534210 A | 12/2014 |
| JP | 2017509688 A | 4/2017 |
| RU | 2612138 C2 | 3/2017 |
| WO | 9504045 A1 | 2/1995 |
| WO | 2012168350 A1 | 12/2012 |
| WO | 2013060751 A1 | 5/2013 |
| WO | 2014086705 A1 | 6/2014 |
| WO | 2014086805 A1 | 6/2014 |
| WO | 2014086806 A1 | 6/2014 |
| WO | 2014086807 A1 | 6/2014 |
| WO | 2014154612 A1 | 10/2014 |

(Continued)

OTHER PUBLICATIONS

International Search Report and Written Opinion issued in International Application No. PCT/EP2019/066811, dated Aug. 8, 2019, 10 pages.

Search Report for Russian Application No. 2021101106/04(002123), dated Aug. 23, 2022, 2 pages.

Belikov, V.G. (2007) "Pharmaceutical Chemistry", pp. 27-29[13 pages(9 pages of English Translation and 4 pages of Original Copy)].

Communication Pursuant to Article 94(3) EPC, European Application No. 19733484.0, dated Sep. 23, 2022, 6 pages.

(Continued)

*Primary Examiner* — Golam M Shameem
(74) *Attorney, Agent, or Firm* — Mintz, Levin, Cohn, Ferris, Glovsky and Popeo, P.C.

(57) ABSTRACT

The invention relates to a compound of formula (I)

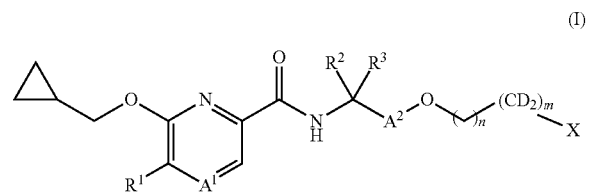

wherein $A^1$, $A^2$, X and $R^1$-$R^3$ are as defined in the description and in the claims. The compound of formula (I) can be used as a medicament.

18 Claims, No Drawings

(56) References Cited

FOREIGN PATENT DOCUMENTS

| WO | 2015150438 A1 | 10/2015 |
| WO | 2015150440 A1 | 10/2015 |
| WO | 2016066534 A1 | 5/2016 |
| WO | 2017097732 A1 | 6/2017 |
| WO | 2018234284 A1 | 12/2018 |
| WO | 2020002320 A1 | 1/2020 |

OTHER PUBLICATIONS

Haider et al. (2020) "Identification and Preclinical Development of a 2,5,6-Trisubstituted Fluorinated Pyridine Derivative as a Radioligand for the Positron Emission Tomography Imaging of Cannabinoid Type 2 Receptors", Journal of Medicinal Chemistry, 63(18):10287-10306.

Haider et al. (2019) "Structure-Activity Relationship Studies of Pyridine-Based Ligands and Identification of a Fluorinated Derivative for Positron Emission Tomography Imaging of Cannabinoid Type 2 Receptors", Journal of Medicinal Chemistry, 62(24):11165-11181.

Slavik et al. (May 7, 2015) "Discovery of a High Affinity and Selective Pyridine Analog as a Potential Positron Emission Tomography Imaging Agent for Cannabinoid Type 2 Receptor", Journal of Medicinal Chemistry, 58(10):4266-4277.

Pitt et al. (1975) "The Synthesis of Deuterium, Carbon-14, and Carrier-free Tritium Labeled Cannabinoids", Journal of Labelled Compounds, pp. 551-575.

PYRIDINE AND PYRAZINE COMPOUNDS AS INHIBITORS OF CANNABINOID RECEPTOR 2

CROSS-REFERENCE TO RELATED APPLICATIONS

This application is a continuation of International Application No. PCT/EP2019/066811 having an International Filing Date of 25 Jun. 2019, which claims the benefit of priority to European Patent Application No. 18180137.4, filed 27 Jun. 2018, the contents of which applications are hereby incorporated by reference in their entirety.

The present invention relates to organic compounds useful for therapy and/or prophylaxis in a mammal, and in particular to compounds that are preferential agonists of the Cannabinoid Receptor 2.

The invention relates in particular to a compound of formula (I)

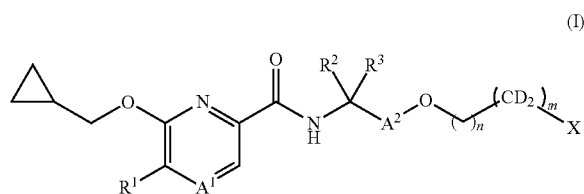

wherein
$R^1$ is alkoxyazetidinyl, dihaloazetidinyl or pyrrolidinyl;
$R^2$ and $R^3$ are independently selected from hydrogen and alkyl;
$A^1$ is —CH— or nitrogen;
$A^2$ is —CH$_2$— or carbonyl;
X is halogen;
n is 0 to 3; and
m is 0 or 1;
provided that m and n are not both 0 at the same time;
or a pharmaceutically acceptable salt thereof.

Novel pyridine and pyrazine derivatives that have high affinity and great selectivity towards the cannabinoid CB2 receptor have been found. These compounds have a modulatory effect on the activity of the CB2 receptor. The term 'modulatory effect' especially means agonist, antagonist and/or inverse agonist effects.

Agonists of the Cannabinoid Receptor 2 are useful for therapy and/or prophylaxis in a mammal. The compound of formula (I) is particularly useful in the treatment or prophylaxis of e.g. pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia/infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

Inverse agonists of the Cannabinoid Receptor 2 are useful for therapy and/or prophylaxis in a mammal.

The compound of formula (I) is particularly useful in the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis and allergy.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

Modulators of the Cannabinoid Receptor 2 are useful for therapy and/or prophylaxis in a mammal.

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemicpreconditioning.

Recent data indicates that endocannabinnoids and their receptors, in particular CB2 might be involved in preconditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

Inverse agonists of the Cannabinoid Receptor 2 are useful for therapy and/or prophylaxis in a mammal.

The compound of formula (I) is particularly useful in the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis and allergy.

The interest in CB2 receptor ligands has been steadily on the rise during the last decade (currently 30-40 patent applications/year). Evidence from different sources support the view that lipid endocannabinoid signaling through CB2 receptors represents an aspect of the mammalian protective armamentarium (Pacher, P. Prog Lipid Res 2011, 50, 193). Its modulation by either selective CB2 receptor agonists or inverse agonists/antagonists (depending on the disease and its stage) holds unique therapeutic potential in a huge number of diseases. For CB2 inverse agonists/antagonists therapeutic opportunities have been demonstrated for many pathological conditions including pain (Pasquini, S. J Med Chem 2012, 55(11): 5391), neuropathic pain (Garcia-Gutierrez, M. S. Br J Pharmacol 2012, 165(4): 951), psychiatric disorders (Garcia-Gutierrez, M. S. Br J Pharmacol 2012, 165(4): 951), psychosis (Garcia-Gutierrez, M. S. Br J Pharmacol 2012, 165(4): 951), osteoporosis and inflammation (Sophocleous, A. Calcif Tissue Int 2008, 82(Suppl. 1):Abst OC18), psychiatric diseases and psychosis (Garcia-Gutierrez, M. S. Br J Pharmacol 2012, 165(4): 951), oncology (Preet, A. Cancer Prev Res 2011, 4: 65), encephalitis and malaria (Zimmer, A. WO 2011045068), allergy and inflammation (Ueda, Y. Life Sci 2007, 80(5): 414), encephalitis and malaria (Zimmer, WO 2011045068), asthma (Lunn, C. A. J Pharmacol Exp Ther 2006, 316(2): 780), immunological disorders (Fakhfouri, G. Neuropharmacology 2012, 63(4): 653), rheumatoid arthritis (Chackalamannil, S. U.S. Pat. No. 7,776,889), arthritis (Lunn, C. A. J Pharmacol Exp Ther 2006, 316(2): 780), and gastrointestinal disorders (Barth, F. FR 2887550).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl, isopropyl, butyl, isobutyl, tert.-butyl and pentyl. Methyl, ethyl and propyl are particular examples of "alkyl" in the compound of formula (I).

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. A particular examples of "alkoxy" is methoxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens. Fluoro is a particular halogen.

The term "carbonyl", alone or in combination, signifies the —C(O)— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereo, isomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to:

A compound according to the invention wherein $R^1$ is methoxyazetidinyl, difluoroazetidinyl or pyrrolidinyl.

A compound according to the invention wherein $R^2$ and $R^3$ are independently selected from hydrogen, ethyl and butyl.

A compound according to the invention wherein $R^2$ and $R^3$ are both ethyl at the same time, or one of $R^2$ and $R^3$ is hydrogen and the other one is butyl.

A compound according to the invention wherein $A^1$ is —CH—.

A compound according to the invention wherein X is fluorine; and A compound according to the invention wherein n is 1, 2 or 3.

The invention further relates to a compound or formula (I) selected from:

fluoromethyl 2-{[6-(cyclopropylmethoxy)-5-(3-methoxyazetidin-1-yl)pyridine-2-carbonyl]amino}-2-ethylbutanoate;
2-fluoroethyl 2-{[6-(cyclopropylmethoxy)-5-(3-methoxyazetidin-1-yl)pyridine-2-carbonyl]amino}-2-ethylbutanoate;
3-fluoropropyl 2-{[6-(cyclopropylmethoxy)-5-(3-methoxyazetidin-1-yl)pyridine-2-carbonyl]amino}-2-ethylbutanoate;
fluoromethyl 2-{[6-(cyclopropylmethoxy)-5-(3,3-difluoroazetidin-1-yl)pyridine-2-carbonyl]amino}-2-ethylbutanoate;
2-fluoroethyl 2-{[6-(cyclopropylmethoxy)-5-(3,3-difluoroazetidin-1-yl)pyridine-2-carbonyl]amino}-2-ethylbutanoate;
3-fluoropropyl 2-{[6-(cyclopropylmethoxy)-5-(3,3-difluoroazetidin-1-yl)pyridine-2-carbonyl]amino}-2-ethylbutanoate;
3-fluoropropyl 2-{[6-(cyclopropylmethoxy)-5-(pyrrolidin-1-yl)pyridine-2-carbonyl]amino}-2-ethylbutanoate;
fluoromethyl 2-{[6-(cyclopropylmethoxy)-5-(pyrrolidin-1-yl)pyridine-2-carbonyl]amino}-2-ethylbutanoate;
2-fluoroethyl 2-{[6-(cyclopropylmethoxy)-5-(pyrrolidin-1-yl)pyridine-2-carbonyl]amino}-2-ethylbutanoate;
fluoromethyl N-[6-(cyclopropylmethoxy)-5-(3-methoxyazetidin-1-yl)pyridine-2-carbonyl]-L-leucinate;
2-fluoroethyl N-[6-(cyclopropylmethoxy)-5-(3-methoxyazetidin-1-yl)pyridine-2-carbonyl]-L-leucinate;
3-fluoropropyl N-[6-(cyclopropylmethoxy)-5-(3-methoxyazetidin-1-yl)pyridine-2-carbonyl]-L-leucinate;
fluoromethyl N-[6-(cyclopropylmethoxy)-5-(pyrrolidin-1-yl)pyridine-2-carbonyl]-L-leucinate;
2-fluoroethyl N-[6-(cyclopropylmethoxy)-5-(pyrrolidin-1-yl)pyridine-2-carbonyl]-L-leucinate;
3-fluoropropyl N-[6-(cyclopropylmethoxy)-5-(pyrrolidin-1-yl)pyridine-2-carbonyl]-L-leucinate;
6-(cyclopropylmethoxy)-N-[(2S)-1-(fluoromethoxy)-4-methylpentan-2-yl]-5-(pyrrolidin-1-yl)pyridine-2-carboxamide;
6-(cyclopropylmethoxy)-N-[(2R)-1-(2-fluoroethoxy)-4-methylpentan-2-yl]-5-(pyrrolidin-1-yl)pyridine-2-carboxamide;
6-(cyclopropylmethoxy)-N-[(2S)-1-(2-fluoroethoxy)-4-methylpentan-2-yl]-5-(pyrrolidin-1-yl)pyridine-2-carboxamide;
6-(cyclopropylmethoxy)-N-[(2S)-1-(3-fluoropropoxy)-4-methylpentan-2-yl]-5-(pyrrolidin-1-yl)pyridine-2-carboxamide;
6-(cyclopropylmethoxy)-N-[(2S)-1-(fluoromethoxy)-3-methylbutan-2-yl]-5-(pyrrolidin-1-yl)pyridine-2-carboxamide;
6-(cyclopropylmethoxy)-N-[(2S)-1-(2-fluoroethoxy)-3-methylbutan-2-yl]-5-(pyrrolidin-1-yl)pyridine-2-carboxamide;
6-(cyclopropylmethoxy)-N-[(2S)-1-(3-fluoropropoxy)-3-methylbutan-2-yl]-5-(pyrrolidin-1-yl)pyridine-2-carboxamide;
6-(cyclopropylmethoxy)-N-[(2S)-1-(fluoromethoxy)propan-2-yl]-5-(pyrrolidin-1-yl)pyridine-2-carboxamide;
6-(cyclopropylmethoxy)-N-[(2S)-1-(2-fluoroethoxy)propan-2-yl]-5-(pyrrolidin-1-yl)pyridine-2-carboxamide;
6-(cyclopropylmethoxy)-N-[(2S)-1-(3-fluoropropoxy)propan-2-yl]-5-(pyrrolidin-1-yl)pyridine-2-carboxamide;
6-(cyclopropylmethoxy)-N-[(2S)-1-(fluoromethoxy)-4-methylpentan-2-yl]-5-(3-methoxyazetidin-1-yl)pyridine-2-carboxamide;
6-(cyclopropylmethoxy)-5-(3,3-difluoroazetidin-1-yl)-N-[(2S)-1-(2-fluoroethoxy)-4-methylpentan-2-yl]pyridine-2-carboxamide;
6-(cyclopropylmethoxy)-N-[(2R)-1-(2-fluoroethoxy)-4-methylpentan-2-yl]-5-(3-methoxyazetidin-1-yl)pyridine-2-carboxamide;
6-(cyclopropylmethoxy)-N-[(2S)-1-(2-fluoroethoxy)-4-methylpentan-2-yl]-5-(3-methoxyazetidin-1-yl)pyridine-2-carboxamide;
6-(cyclopropylmethoxy)-N-[(2S)-1-(3-fluoropropoxy)-4-methylpentan-2-yl]-5-(3-methoxyazetidin-1-yl)pyridine-2-carboxamide;
6-(cyclopropylmethoxy)-N-[(2S)-1-(fluoromethoxy)-3-methylbutan-2-yl]-5-(3-methoxyazetidin-1-yl)pyridine-2-carboxamide;
6-(cyclopropylmethoxy)-N-[(2S)-1-(2-fluoroethoxy)-3-methylbutan-2-yl]-5-(3-methoxyazetidin-1-yl)pyridine-2-carboxamide;

6-(cyclopropylmethoxy)-N-[(2S)-1-(3-fluoropropoxy)-3-methylbutan-2-yl]-5-(3-methoxyazetidin-1-yl)pyridine-2-carboxamide;

6-(cyclopropylmethoxy)-N-[(2S)-1-(2-fluoroethoxy)propan-2-yl]-5-(3-methoxyazetidin-1-yl)pyridine-2-carboxamide;

6-(cyclopropylmethoxy)-N-[(2S)-1-(3-fluoropropoxy)propan-2-yl]-5-(3-methoxyazetidin-1-yl)pyridine-2-carboxamide;

6-(cyclopropylmethoxy)-N-{3-[(fluoromethoxy)methyl]pentan-3-yl}-5-(pyrrolidin-1-yl)pyridine-2-carboxamide;

6-(cyclopropylmethoxy)-N-{3-[(2-fluoroethoxy)methyl]pentan-3-yl}-5-(pyrrolidin-1-yl)pyridine-2-carboxamide;

6-(cyclopropylmethoxy)-N-{3-[(3-fluoropropoxy)methyl]pentan-3-yl}-5-(pyrrolidin-1-yl)pyridine-2-carboxamide;

6-(cyclopropylmethoxy)-N-{3-[(fluoromethoxy)methyl]pentan-3-yl}-5-(3-methoxyazetidin-1-yl)pyridine-2-carboxamide;

6-(cyclopropylmethoxy)-N-{3-[(2-fluoroethoxy)methyl]pentan-3-yl}-5-(3-methoxyazetidin-1-yl)pyridine-2-carboxamide;

6-(cyclopropylmethoxy)-N-{3-[(3-fluoropropoxy)methyl]pentan-3-yl}-5-(3-methoxyazetidin-1-yl)pyridine-2-carboxamide;

fluoromethyl 2-{[6-(cyclopropylmethoxy)-5-(3-methoxyazetidin-1-yl)pyrazine-2-carbonyl]amino}-2-ethylbutanoate;

2-fluoroethyl 2-{[6-(cyclopropylmethoxy)-5-(3-methoxyazetidin-1-yl)pyrazine-2-carbonyl]amino}-2-ethylbutanoate;

3-fluoropropyl 2-{[6-(cyclopropylmethoxy)-5-(3-methoxyazetidin-1-yl)pyrazine-2-carbonyl]amino}-2-ethylbutanoate;

fluoro(dideuterio)methyl 2-{[6-(cyclopropylmethoxy)-5-(3-methoxyazetidin-1-yl)pyridine-2-carbonyl]amino}-2-ethylbutanoate;

2-fluoro(2,2-dideuterio)ethyl 2-{[6-(cyclopropylmethoxy)-5-(3-methoxyazetidin-1-yl)pyridine-2-carbonyl]amino}-2-ethylbutanoate;

3-fluoro(3,3-dideuterio)propyl 2-{[6-(cyclopropylmethoxy)-5-(3-methoxyazetidin-1-yl)pyridine-2-carbonyl]amino}-2-ethylbutanoate;

fluoro(dideuterio)methyl 2-{[6-(cyclopropylmethoxy)-5-(3,3-difluoroazetidin-1-yl)pyridine-2-carbonyl]amino}-2-ethylbutanoate;

2-fluoro(2,2-dideuterio)ethyl 2-{[6-(cyclopropylmethoxy)-5-(3,3-difluoroazetidin-1-yl)pyridine-2-carbonyl]amino}-2-ethylbutanoate;

3-fluoro(3,3-dideuterio)propyl 2-{[6-(cyclopropylmethoxy)-5-(3,3-difluoroazetidin-1-yl)pyridine-2-carbonyl]amino}-2-ethylbutanoate;

3-fluoro(3,3-dideuterio)propyl 2-{[6-(cyclopropylmethoxy)-5-(pyrrolidin-1-yl)pyridine-2-carbonyl]amino}-2-ethylbutanoate;

fluoro(dideuterio)methyl 2-{[6-(cyclopropylmethoxy)-5-(pyrrolidin-1-yl)pyridine-2-carbonyl]amino}-2-ethylbutanoate;

2-fluoro(2,2-dideuterio)ethyl 2-{[6-(cyclopropylmethoxy)-5-(pyrrolidin-1-yl)pyridine-2-carbonyl]amino}-2-ethylbutanoate;

6-(cyclopropylmethoxy)-N-[(2S)-1-{[fluoro(dideuterio)methyl]oxy}-4-methylpentan-2-yl]-5-(pyrrolidin-1-yl)pyridine-2-carboxamide;

6-(cyclopropylmethoxy)-N-[(2S)-1-{[2-fluoro(2,2-dideuterio)ethyl]oxy}-4-methylpentan-2-yl]-5-(pyrrolidin-1-yl)pyridine-2-carboxamide;

6-(cyclopropylmethoxy)-N-[(2S)-1-{[3-fluoro(3,3-dideuterio)propyl]oxy}-4-methylpentan-2-yl]-5-(pyrrolidin-1-yl)pyridine-2-carboxamide;

6-(cyclopropylmethoxy)-N-[(2S)-1-{[fluoro(dideuterio)methyl]oxy}-3-methylbutan-2-yl]-5-(pyrrolidin-1-yl)pyridine-2-carboxamide;

6-(cyclopropylmethoxy)-N-[(2S)-1-{[2-fluoro(2,2-dideuterio)ethyl]oxy}-3-methylbutan-2-yl]-5-(pyrrolidin-1-yl)pyridine-2-carboxamide;

6-(cyclopropylmethoxy)-N-[(2S)-1-{[3-fluoro(3,3-dideuterio)propyl]oxy}-3-methylbutan-2-yl]-5-(pyrrolidin-1-yl)pyridine-2-carboxamide;

6-(cyclopropylmethoxy)-N-[(2S)-1-{[fluoro(dideuterio)methyl]oxy}propan-2-yl]-5-(pyrrolidin-1-yl)pyridine-2-carboxamide;

6-(cyclopropylmethoxy)-N-[(2S)-1-{[2-fluoro(2,2-dideuterio)ethyl]oxy}propan-2-yl]-5-(pyrrolidin-1-yl)pyridine-2-carboxamide;

6-(cyclopropylmethoxy)-N-[(2S)-1-{[3-fluoro(3,3-dideuterio)propyl]oxy}propan-2-yl]-5-(pyrrolidin-1-yl)pyridine-2-carboxamide;

6-(cyclopropylmethoxy)-N-[(2S)-1-{[fluoro(dideuterio)methyl]oxy}-4-methylpentan-2-yl]-5-(3-methoxyazetidin-1-yl)pyridine-2-carboxamide;

6-(cyclopropylmethoxy)-N-[(2S)-1-{[2-fluoro(2,2-dideuterio)ethyl]oxy}-4-methylpentan-2-yl]-5-(3-methoxyazetidin-1-yl)pyridine-2-carboxamide;

6-(cyclopropylmethoxy)-N-[(2S)-1-{[3-fluoro(3,3-dideuterio)propyl]oxy}-4-methylpentan-2-yl]-5-(3-methoxyazetidin-1-yl)pyridine-2-carboxamide;

6-(cyclopropylmethoxy)-N-[(2S)-1-{[fluoro(dideuterio)methyl]oxy}-3-methylbutan-2-yl]-5-(3-methoxyazetidin-1-yl)pyridine-2-carboxamide;

6-(cyclopropylmethoxy)-N-[(2S)-1-{[2-fluoro(2,2-dideuterio)ethyl]oxy}-3-methylbutan-2-yl]-5-(3-methoxyazetidin-1-yl)pyridine-2-carboxamide;

6-(cyclopropylmethoxy)-N-[(2S)-1-{[3-fluoro(3,3-dideuterio)propyl]oxy}-3-methylbutan-2-yl]-5-(3-methoxyazetidin-1-yl)pyridine-2-carboxamide;

6-(cyclopropylmethoxy)-N-[(2S)-1-{[2-fluoro(2,2-dideuterio)ethyl]oxy}propan-2-yl]-5-(3-methoxyazetidin-1-yl)pyridine-2-carboxamide;

6-(cyclopropylmethoxy)-N-[(2S)-1-{[3-fluoro(3,3-dideuterio)propyl]oxy}propan-2-yl]-5-(3-methoxyazetidin-1-yl)pyridine-2-carboxamide;

6-(cyclopropylmethoxy)-N-[3-({[fluoro(dideuterio)methyl]oxy}methyl)pentan-3-yl]-5-(pyrrolidin-1-yl)pyridine-2-carboxamide;

6-(cyclopropylmethoxy)-N-[3-({[2-fluoro(2,2-dideuterio)ethyl]oxy}methyl)pentan-3-yl]-5-(pyrrolidin-1-yl)pyridine-2-carboxamide;

6-(cyclopropylmethoxy)-N-[3-({[3-fluoro(3,3-dideuterio)propyl]oxy}methyl)pentan-3-yl]-5-(pyrrolidin-1-yl)pyridine-2-carboxamide;

6-(cyclopropylmethoxy)-N-[3-({[fluoro(dideuterio)methyl]oxy}methyl)pentan-3-yl]-5-(3-methoxyazetidin-1-yl)pyridine-2-carboxamide;

6-(cyclopropylmethoxy)-N-[3-({[2-fluoro(2,2-dideuterio)ethyl]oxy}methyl)pentan-3-yl]-5-(3-methoxyazetidin-1-yl)pyridine-2-carboxamide;

6-(cyclopropylmethoxy)-N-[3-({[3-fluoro(3,3-dideuterio)propyl]oxy}methyl)pentan-3-yl]-5-(3-methoxyazetidin-1-yl)pyridine-2-carboxamide;

ethyl 2-{[6-(cyclopropylmethoxy)-5-(3-methoxyazetidin-1-yl)pyridine-2-carbonyl]amino}-2-ethyl-4-fluoro(4,4-dideuterio)butanoate;

ethyl 2-{[6-(cyclopropylmethoxy)-5-(3-methoxyazetidin-1-yl)pyridine-2-carbonyl]amino}-2-ethyl-4-fluoro(4,4-dideuterio)butanoate;
6-(cyclopropylmethoxy)-5-(3-fluoro-3-methylazetidin-1-yl)-N-(3-(3-fluoropropylcarbamoyl)pentan-3-yl)picolinamide;
ethyl 2-{[6-(cyclopropylmethoxy)-5-(3-methoxyazetidin-1-yl)pyridine-2-carbonyl]amino}-2-ethyl-4-fluorobutanoate;
ethyl 2-{[6-(cyclopropylmethoxy)-5-(3-methoxyazetidin-1-yl)pyridine-2-carbonyl]amino}-2-ethyl-3-fluorobutanoate;
ethyl 2-{[6-(cyclopropylmethoxy)-5-(3-methoxyazetidin-1-yl)pyridine-2-carbonyl]amino}-2-ethyl-4-fluorobutanoate; and
ethyl 2-{[6-(cyclopropylmethoxy)-5-(3-methoxyazetidin-1-yl)pyridine-2-carbonyl]amino}-2-ethyl-3-fluorobutanoate.

The invention further relates to a compound according to the invention selected from:
2-fluoroethyl 2-{[6-(cyclopropylmethoxy)-5-(3-methoxyazetidin-1-yl)pyridine-2-carbonyl]amino}-2-ethylbutanoate;
3-fluoropropyl 2-{[6-(cyclopropylmethoxy)-5-(3-methoxyazetidin-1-yl)pyridine-2-carbonyl]amino}-2-ethylbutanoate;
2-fluoroethyl N-[6-(cyclopropylmethoxy)-5-(3-methoxyazetidin-1-yl)pyridine-2-carbonyl]-L-leucinate;
2-fluoroethyl N-[6-(cyclopropylmethoxy)-5-(pyrrolidin-1-yl)pyridine-2-carbonyl]-L-leucinate;
6-(cyclopropylmethoxy)-N-[(2S)-1-(fluoromethoxy)-4-methylpentan-2-yl]-5-(pyrrolidin-1-yl)pyridine-2-carboxamide;
6-(cyclopropylmethoxy)-N-[(2S)-1-(2-fluoroethoxy)-4-methylpentan-2-yl]-5-(pyrrolidin-1-yl)pyridine-2-carboxamide;
6-(cyclopropylmethoxy)-N-[(2S)-1-(fluoromethoxy)-4-methylpentan-2-yl]-5-(3-methoxyazetidin-1-yl)pyridine-2-carboxamide;
6-(cyclopropylmethoxy)-5-(3,3-difluoroazetidin-1-yl)-N-[(2S)-1-(2-fluoroethoxy)-4-methylpentan-2-yl]pyridine-2-carboxamide; and
6-(cyclopropylmethoxy)-N-[(2S)-1-(2-fluoroethoxy)-4-methylpentan-2-yl]-5-(3-methoxyazetidin-1-yl)pyridine-2-carboxamide.

The invention also relates in particular to 6-(cyclopropylmethoxy)-N-[(2S)-1-(2-fluoroethoxy)-4-methylpentan-2-yl]-5-(pyrrolidin-1-yl)pyridine-2-carboxamide.

The synthesis of the compounds with the general structure I can, for example, be accomplished according to the following schemes.

Following the procedure according to scheme 1, compound AA (R'=H, methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be used as starting material. AA is either commercially available, described in the literature or can be synthesized by a person skilled in the art.

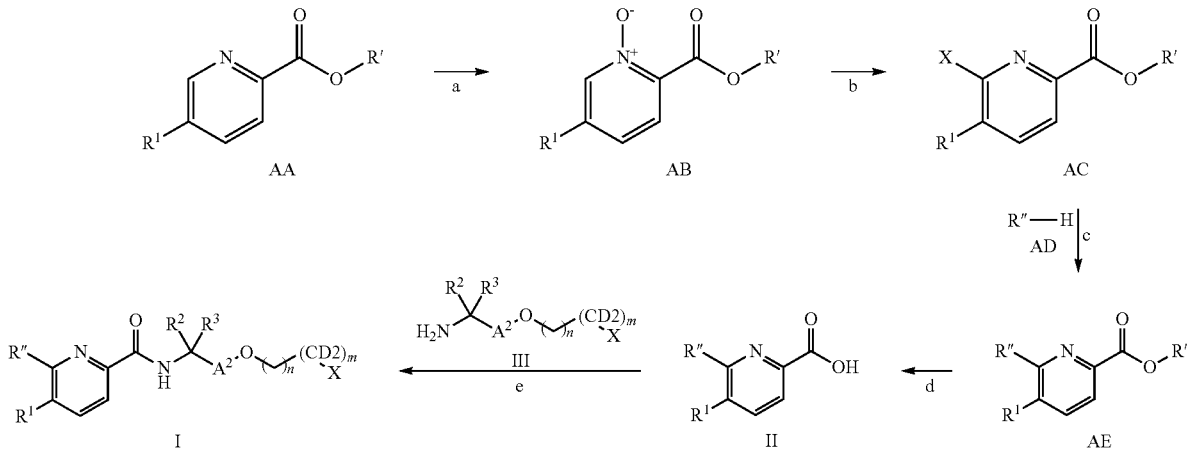

Scheme 1

Compound AB can be prepared from AA by oxidation with a suitable oxidizing reagent under conditions known to a person skilled in the art (step a), e.g. by treatment with 3-chloro perbenzoic acid in dichloromethane at ambient temperature.

Conversion of compound AB to 6-chloro or 6-bromo-picoline AC (X=Cl, Br) can be achieved e.g. by treatment with phosphoryl trichloride or tribromide either without an additional solvent or in a suitable solvent such as chloroform at temperatures between 20° C. and the boiling point of the solvent, or by using other conditions known in the literature (step b).

6-Chloro- or bromo-picoline AC (X=Cl, Br) can be transformed to compound AE by reaction with a suitably substituted primary or secondary alcohol AD such as cyclopropylmethanol in the presence of a base, for example sodium hydride, with or without an inert solvent, for example dimethylformamide, at temperatures ranging from room temperature to the reflux temperature of the solvent, particularly at room temperature (step c).

The saponification of the ester of general formula AE (R'≠H) by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to an acid of general formula II (step d).

Compound I (R"=cyclopropylmethyloxy) can be prepared from II and the corresponding amine of formula III by suitable amide bond forming reactions (step e). These reactions are known in the art. For example coupling reagents like N,N'-carbonyl-diimidazole (CDI), N,N'-dicyclohexyl-carbodiimide (DCC), 1-(3-dimethylaminopropyl)-3-ethyl-carbodiimide hydrochloride (EDCI), 1-[bis(dimethyl-amino)-methylene]-1H-1,2,3-triazolo[4,5-b]pyridinium-3-oxide hexafluorophosphate (HATU), 1-hydroxy-1,2,3-benzotriazole (HOBT), 0-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example N-methylmorpholine in an inert solvent such as for example dimethylformamide at room temperature.

Alternatively, compound AC (R'=methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be: i) converted into its acid congener AC (R'=H) as described in step d; ii) transformed into the corresponding amide by treatment with amine III as described in step e; and iii) reacted with alcohol AD as described in step c to arrive at compound I.

Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae AA to AE, AD, II or III contain chiral centers, picolines of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 2, compound BA (R'=H, methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be used as starting material. BA is either commercially available (e.g. for R'=methyl: 5-bromo-6-chloro-pyridine-2-carboxylic acid methyl ester CAN 1214353-79-3), described in the literature or can be synthesized by a person skilled in the art.

Scheme 2

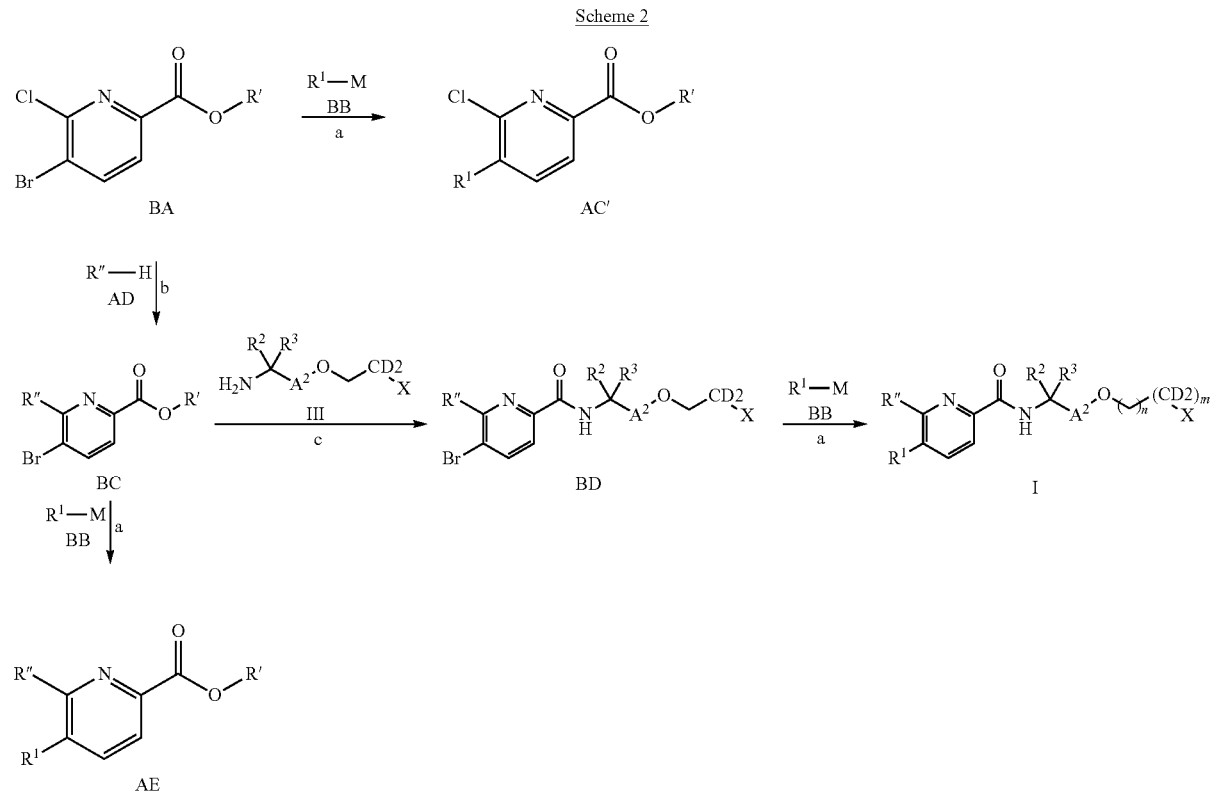

Amines III and alcohols AD are either commercially available, described in the literature, can be synthesized by a person skilled in the art or as described in the experimental part.

If one of the starting materials, compounds of formulae AA, AD or III, contains one or more functional groups which are not stable or are reactive under the reaction conditions of one or more reaction steps, appropriate protecting groups (P) (as described e.g. in T. W. Greene et al., Compound AC' can be prepared from BA by coupling with an amine BB (M is H) by methods well known to a person skilled in the art, e.g. using a palladium catalyst such as tris(dibenzylideneacetone)dipalladium/dimethylbisdiphenyl-phosphinoxanthene and a base such as cesium carbonate in a solvent such as 1,4-dioxane, preferentially at the boiling point of the solvent (step a).

Compound AC' can be further elaborated to compound I (R"=cyclopropylmethyloxy) by: i) reaction with compound AD to form compound AE as described in step c of scheme 1; ii) saponification as described in step d of scheme 1; and iii) amide bond formation as described in step e of scheme 1.

Furthermore, compound BA can be converted into compound BC by treatment with compound AD as described in step c of scheme 1 (step b).

Subsequent transformation of compound BC into compound AE can be achieved as discussed for the conversion of BA into AC' (step a).

Compound AE can be further elaborated to compound I (R"=cyclopropylmethyloxy) by: i) saponification as described in step d of scheme 1; ii) amide bond formation as described in step e of scheme 1.

Alternatively, compound BC (R'=methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) can be: i) converted into its acid congener BC (R'=H) as described in step d of scheme 1; ii) transformed into the corresponding amide BD by treatment with amine III as described in step e of scheme 1; and iii) reacted with BB as described in step a to arrive at compound I (R"=cyclopropylmethyloxy).

Furthermore, compound I can also be synthesized applying the following reaction sequence: i) saponification of compound BA (R'=methyl, ethyl, isopropyl, tert. butyl or another suitable protecting group described for example in T. W. Greene et al., Protective Groups in Organic Chemistry, John Wiley and Sons Inc. New York 1999, 3$^{rd}$ edition) to its acid congener BA (R'=H) as described in step d of scheme 1; ii) conversion to the corresponding amide by treatment with amine III as described in step e of scheme 1; iii) reaction with compound BB as described in step a; and iv) reaction with compound AD as described in step b. Optionally step iii) and step iv) can be interchanged.

If one of the starting materials, compounds of formulae CA, CB or BC contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae BA, BB or AD contain chiral centers, picolines of formula AC' and AE can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention also relates to a process for the preparation of a compound of formula (I) comprising one of the following steps:

(a) the reaction of a compound of formula (A)

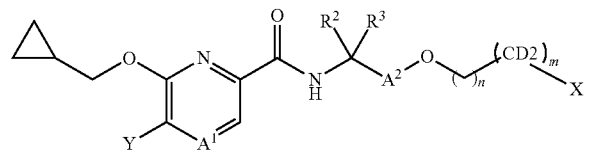

(A)

in the presence of R$^1$—H, a palladium catalyst and a base;
(b) the reaction of a compound of formula (B)

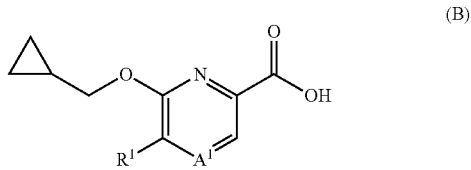

(B)

in the presence of NH$_2$—C(R$^2$R$^3$)-A$^2$-O—(CH$_2$)$_n$—(CD$_2$)$_m$-X, a coupling agent and a base;
wherein A$^1$, A$^2$, X, R$^1$-R$^3$, m and n are as defined above and Y is halogen.

The coupling agent of step (b) is conveniently an amide bond forming agent, like e.g. N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), 0-benzotriazol-1-yl-N,N,N',N'-tetramethyluronium tetrafluoroborate (TBTU) or and O-benzotriazole-N,N,N',N'-tetramethyl-uronium-hexafluoro-phosphate (HBTU).

N-methylmorpholine is a convenient base for step (b).

HBTU can advantageously be used in combination with N-methylmorpholine in step (b).

The solvent of step (b) can advantageously be dimethylformamide.

In step (a), the palladium catalyst can be for example tris(dibenzylideneacetone)dipalladium/dimethylbisdiphenyl-phosphinoxanthene.

In step (a) the base can be e.g. cesium carbonate.
In step (a), the solvent is advantageously 1,4-dioxane.
In step (a), Y can conveniently be bromine.

The invention also relates to a compound according to the invention when manufactured according to a process of the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention also relates in particular to:

The use of a compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

A compound of formula (I) for use in the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis; and A method for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention will now be illustrated by the following examples which have no limiting character.

EXAMPLES

Abbreviations

CAN=chemical abstracts service number; DIPEA=N-ethyl-N-isopropylpropan-2-amine; DMF=dimethylformamide; EtOAc=ethyl acetate; hept.=heptane; HPLC=LC=high performance liquid chromatography; ISP=ion spray, corresponds to ESI (electrospray); MS=mass spectrometry; NMR data are reported in parts per million (δ) relative to internal tetramethylsilane and are referenced to the deuterium lock signal from the sample solvent ($d_6$-DMSO unless otherwise stated); coupling constants (J) are in Hertz; RT=room temperature; TBTU=O-(benzotriazol-1-yl)-N,N,N',N'-tetramethyl-uronium-tetrafluoroborate; THF=tetrahydrofuran; tlc=thin layer chromatography.

Example 1

Fluoromethyl 2-{[6-(cyclopropylmethoxy)-5-(3-methoxyazetidin-1-yl)pyridine-2-carbonyl]amino}-2-ethylbutanoate

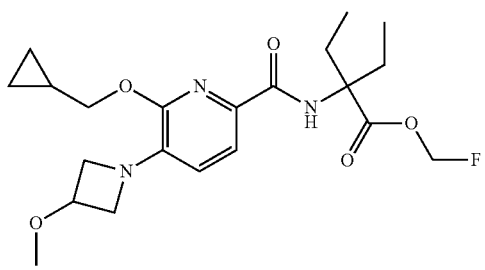 [SMILES: CCC(CC)(NC(=O)c1ccc(N2CC(OC)C2)c(OCC2CC2)n1)C(=O)OCF]

a) 2-(6-(Cyclopropylmethoxy)-5-(3-methoxyazetidin-1-yl)picolinamido)-2-ethylbutanoic acid

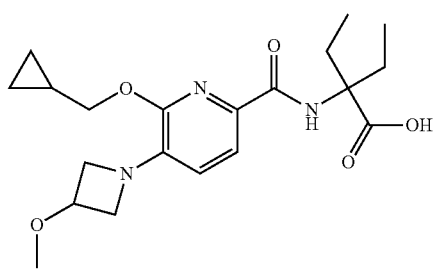 [SMILES: CCC(CC)(NC(=O)c1ccc(N2CC(OC)C2)c(OCC2CC2)n1)C(=O)O]

In a 25 mL round-bottomed flask, ethyl 2-(6-(cyclopropylmethoxy)-5-(3-methoxyazetidin-1-yl)picolinamido)-2-ethylbutanoate (CAN 1778678-14-0, 210 mg, 501 µmol, Eq: 1) was combined with THF (3 mL) and MeOH (3.3 mL) to give a colorless solution. KOH (140 mg, 2.5 mmol, Eq: 5), dissolved in water (3 mL) was added and the reaction mixture was stirred at 100° C. for 19 h. KOH (75 mg) and 1 mL THF, MeOH and water were added and stirring was continued at 100° C. for 3 h. The organic solvent was removed under reduced pressure and the aqueous phase was acidified (1 N HCl). The resulting white suspension was extracted with EtOAc (3×25 mL). The combined organic layers were washed with brine (1×20 mL), dried over $Na_2SO_4$ and concentrated in vacuo to give the crude title compound as light brown oil which was used in the next step without further purification, MS (ISP): 392.314 [MH$^+$].

b) Fluoromethyl 2-{[6-(cyclopropylmethoxy)-5-(3-methoxyazetidin-1-yl)pyridine-2-carbonyl]amino}-2-ethylbutanoate In a 10 mL round-bottomed flask, 2-(6-(cyclopropylmethoxy)-5-(3-methoxyazetidin-1-yl)picolinamido)-2-ethylbutanoic acid (37 mg, 94.5 µmol, Eq: 1) was combined with DMF (500 µL) to give a light brown solution. $K_2CO_3$ (65.3 mg, 473 µmol, Eq: 5) and fluoro-iodo-methane (76.3 mg, 32.2 µL, 473 µmol, Eq: 5) were added. The reaction mixture was stirred at RT for 30 min, diluted with EtOAc and washed with sat. NaCl (3×10 mL). The organic layer was dried over $Na_2SO_4$ and concentrated in vacuo. The crude product was purified by column chromatography ($SiO_2$, 5 g, hept./EtOAc) to give the title compound (27 mg, 68%) as colorless oil, MS (ISP): 424.341 [MH$^+$].

Example 2

2-Fluoroethyl 2-{[6-(cyclopropylmethoxy)-5-(3-methoxyazetidin-1-yl)pyridine-2-carbonyl]amino}-2-ethylbutanoate

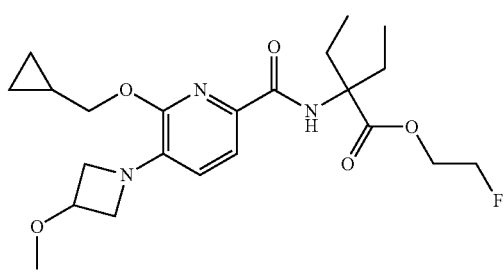 [SMILES: CCC(CC)(NC(=O)c1ccc(N2CC(OC)C2)c(OCC2CC2)n1)C(=O)OCCF]

In analogy to the procedure described in example 1 b, 2-(6-(cyclopropylmethoxy)-5-(3-methoxyazetidin-1-yl)picolinamido)-2-ethylbutanoic acid (example 1 a) was reacted with fluoro-iodo-methane to give the title compound as colorless oil, MS (ISP): 438.346 [MH$^+$].

Example 3

3-Fluoropropyl 2-{[6-(cyclopropylmethoxy)-5-(3-methoxyazetidin-1-yl)pyridine-2-carbonyl]amino}-2-ethylbutanoate

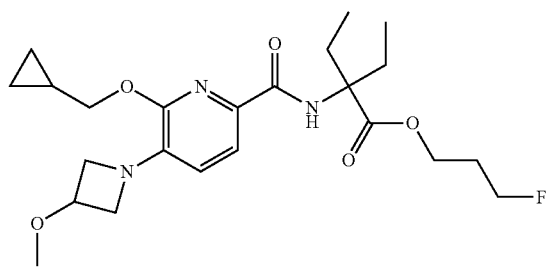 [SMILES: CCC(CC)(NC(=O)c1ccc(N2CC(OC)C2)c(OCC2CC2)n1)C(=O)OCCCF]

In analogy to the procedure described in example 1 b, 2-(6-(cyclopropylmethoxy)-5-(3-methoxyazetidin-1-yl)picolinamido)-2-ethylbutanoic acid (example 1 a) was reacted with 1-iodo-3-fluoropropane to give the title compound as colorless oil, MS (ISP): 452.4 [MH$^+$].

Example 4

Fluoromethyl 2-{[6-(cyclopropylmethoxy)-5-(3,3-difluoroazetidin-1-yl)pyridine-2-carbonyl]amino}-2-ethylbutanoate

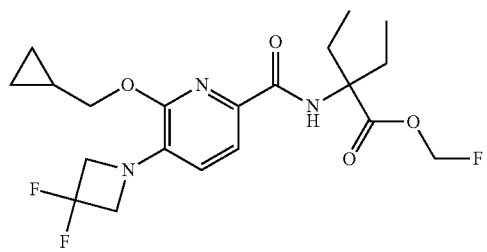 [SMILES: CCC(CC)(NC(=O)c1ccc(N2CC(F)(F)C2)c(OCC2CC2)n1)C(=O)OCF]

In analogy to the procedure described in example 1 b, 2-(6-(cyclopropylmethoxy)-5-(3,3-difluoroazetidin-1-yl)picolinamido)-2-ethylbutanoic acid (CAN 1415896-50-2) was reacted with fluoro-iodo-methane to give the title compound as colorless oil, LC-MS (UV peak area/ESI) 100%, 430.1952 [MH$^+$].

Example 5

2-Fluoroethyl 2-{[6-(cyclopropylmethoxy)-5-(3,3-difluoroazetidin-1-yl)pyridine-2-carbonyl]amino}-2-ethylbutanoate

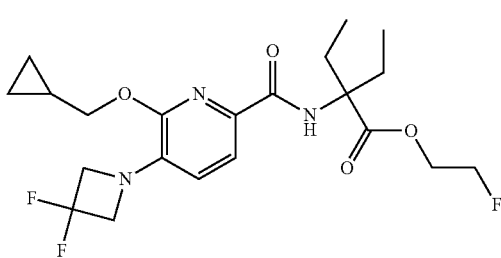 [SMILES: CCC(CC)(NC(=O)c1ccc(N2CC(F)(F)C2)c(OCC2CC2)n1)C(=O)OCCF]

In analogy to the procedure described in example 1 b, 2-(6-(cyclopropylmethoxy)-5-(3,3-difluoroazetidin-1-yl)picolinamido)-2-ethylbutanoic acid (CAN 1415896-50-2) was reacted with fluoro-iodo-ethane to give the title compound as colorless oil, LC-MS (UV peak area/ESI) 100%, 444.2109 [MH$^+$].

Example 6

3-Fluoropropyl 2-{[6-(cyclopropylmethoxy)-5-(3,3-difluoroazetidin-1-yl)pyridine-2-carbonyl]amino}-2-ethylbutanoate

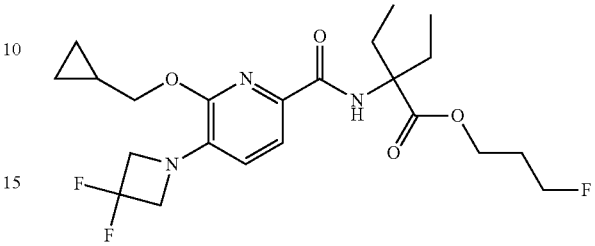

In analogy to the procedure described in example 1 b, 2-(6-(cyclopropylmethoxy)-5-(3,3-difluoroazetidin-1-yl)picolinamido)-2-ethylbutanoic acid (CAN 1415896-50-2) was reacted with 1-iodo-3-fluoropropane to give the title compound as colorless oil, LC-MS (UV peak area/ESI) 100%, 458.2263 [MH$^+$].

Example 7

3-Fluoropropyl 2-{[6-(cyclopropylmethoxy)-5-(pyrrolidin-1-yl)pyridine-2-carbonyl]amino}-2-ethylbutanoate

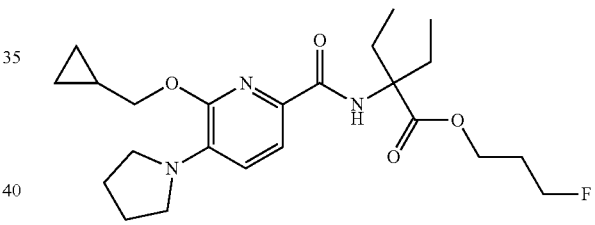

In analogy to the procedure described in example 1 b, 2-(6-(cyclopropylmethoxy)-5-(pyrrolidin-1-yl)picolinamido)-2-ethylbutanoic acid (CAN 1415897-34-5) was reacted with 1-iodo-3-fluoropropane to give the title compound as colorless oil, LC-MS (UV peak area/ESI) 98%, 436.2615 [MH$^+$].

Example 8

Fluoromethyl 2-{[6-(cyclopropylmethoxy)-5-(pyrrolidin-1-yl)pyridine-2-carbonyl]amino}-2-ethylbutanoate

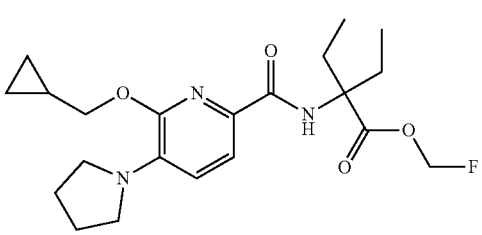 [SMILES: CCC(CC)(NC(=O)c1ccc(N2CCCC2)c(OCC2CC2)n1)C(=O)OCF]

In analogy to the procedure described in example 1 b, 2-(6-(cyclopropylmethoxy)-5-(pyrrolidin-1-yl)picolinamido)-2-ethylbutanoic acid (CAN 1415897-34-5) was reacted with fluoro-iodo-methane to give the title compound as colorless oil, LC-MS (UV peak area/ESI) 96%, 408.2301 [MH+].

Example 9

2-Fluoroethyl 2-{[6-(cyclopropylmethoxy)-5-(pyrrolidin-1-yl)pyridine-2-carbonyl]amino}-2-ethylbutanoate

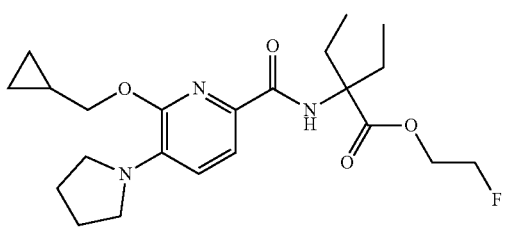 [SMILES: CCC(CC)(NC(=O)c1ccc(N2CCCC2)c(OCC2CC2)n1)C(=O)OCCF]

In analogy to the procedure described in example 1 b, 2-(6-(cyclopropylmethoxy)-5-(pyrrolidin-1-yl)picolinamido)-2-ethylbutanoic acid (CAN 1415897-34-5) was reacted with fluoro-iodo-ethane to give the title compound as colorless oil, LC-MS (UV peak area/ESI) 97%, 422.2463 [MH+].

Example 10

Fluoromethyl N-[6-(cyclopropylmethoxy)-5-(3-methoxyazetidin-1-yl)pyridine-2-carbonyl]-L-leucinate

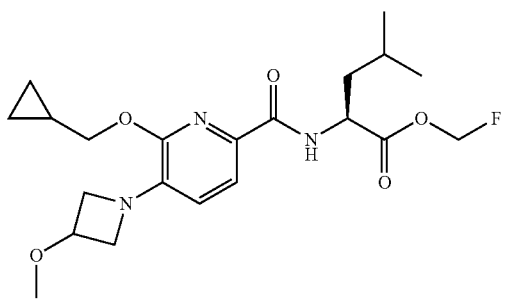 [SMILES: COC1CN(c2ccc(C(=O)N[C@@H](CC(C)C)C(=O)OCF)nc2OCC2CC2)C1]

a) (S)-Methyl 2-(5-bromo-6-(cyclopropylmethoxy)picolinamido)-4-methylpentanoate

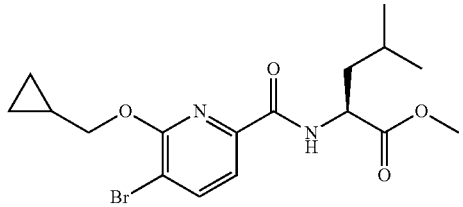 [SMILES: COC(=O)[C@H](CC(C)C)NC(=O)c1ccc(Br)c(OCC2CC2)n1]

In a 100 mL round-bottomed flask, 5-bromo-6-(cyclopropylmethoxy)picolinic acid (CAN 1415898-37-1, 850 mg, 3.12 mmol, Eq: 1) was combined with DMF (15 mL) to give a light yellow solution. TBTU (1.1 g, 3.44 mmol, Eq: 1.1), DIPEA (1.61 g, 2.18 mL, 12.5 mmol, Eq: 4) and L-leucine methyl ester hydrochloride (CAN 7517-19-3, 794 mg, 4.37 mmol, Eq: 1.4) were added and the mixture was stirred at RT for 30 min. The solvent was removed under reduced pressure and the residue dissolved in EtOAc. The organic layers were combined, washed with sat. NaHCO$_3$ (3×20 mL), 1 M HCl (3×20 mL), and sat. NaCl (3×20 mL). The organic layers were dried over Na$_2$SO$_4$ and concentrated in vacuo to obtain crude title product (1.1 g, 88%) as light brown oil which was used in the next reaction step without further purification, MS (ISP): 399.162 [MH+].

b) (S)-Methyl 2-(6-(cyclopropylmethoxy)-5-(3-methoxyazetidin-1-yl)picolinamido)-4-methylpentanoate

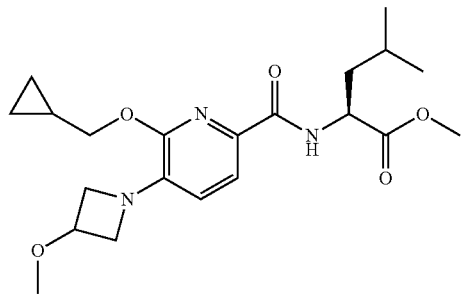 [SMILES: COC(=O)[C@H](CC(C)C)NC(=O)c1ccc(N2CC(OC)C2)c(OCC2CC2)n1]

In a 20 mL sealed tube, (S)-methyl 2-(5-bromo-6-(cyclopropylmethoxy)picolinamido)-4-methylpentanoate (385 mg, 964 µmol, Eq: 1) was combined with toluene (10 mL) to give a colorless solution. 3-Methoxyazetidine hydrochloride (CAN 148644-09-1, 179 mg, 1.45 mmol, Eq: 1.5) and Cs$_2$CO$_3$ (943 mg, 2.89 mmol, Eq: 3) were added. rac-2,2'-Bis(diphenylphosphino)-1,1'-binaphthyl (120 mg, 193 µmol, Eq: 0.2) and palladium(II) acetate (43.3 mg, 193 µmol, Eq: 0.2) were added. The white suspension was heated to 110° C. for 1 h, diluted with EtOAc and filtered through celite. The organic layers were combined, washed with 1 M HCl (3×50 mL) and sat. NaCl (1×100 mL). The organic layers were dried over Na$_2$SO$_4$ and concentrated in vacuo. The crude product was purified by column chromatography (SiO$_2$, 50 g, hept./EtOAc) to give the title compound (287 mg, 73%) as light yellow oil, MS (ISP): 406.319 [MH+].

c) (S)-2-(6-(Cyclopropylmethoxy)-5-(3-methoxyazetidin-1-yl)picolinamido)-4-methylpentanoic acid

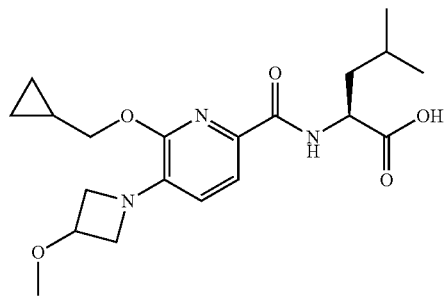 [SMILES: COC1CN(c2ccc(C(=O)N[C@@H](CC(C)C)C(=O)O)nc2OCC2CC2)C1]

In a 25 mL round-bottomed flask, (S)-methyl 2-(6-(cyclopropylmethoxy)-5-(3-methoxyazetidin-1-yl)picolinamido)-4-methylpentanoate (270 mg, 666 μmol, Eq: 1) was combined with THF (2 mL), water (2 mL) and MeOH (2 mL) to give a light yellow solution. KOH (112 mg, 2 mmol, Eq: 3) was added and the mixture was stirred for 1 h at RT. The organic solvent was removed under reduced pressure. The aqueous phase was adjusted to pH 2 with 1 M HCl and extracted with EtOAc (3×20 mL) and brine (1×25 mL). The organic layers were dried over $Na_2SO_4$ and concentrated in vacuo to give crude title compound (quant.) as light brown oil which was used in the next reaction step without further purification, MS (ISP): 392.316 [MH$^+$].

d) Fluoromethyl N-[6-(cyclopropylmethoxy)-5-(3-methoxyazetidin-1-yl)pyridine-2-carbonyl]-L-leucinate In analogy to the procedure described in example 1 b, (S)-2-(6-(cyclopropylmethoxy)-5-(3-methoxyazetidin-1-yl)picolinamido)-4-methylpentanoic acid was reacted with fluoro-iodo-methane to give the title compound as colorless oil, MS (ISP): 424.289 [MH$^+$].

Example 11

2-Fluoroethyl N-[6-(cyclopropylmethoxy)-5-(3-methoxyazetidin-1-yl)pyridine-2-carbonyl]-L-leucinate

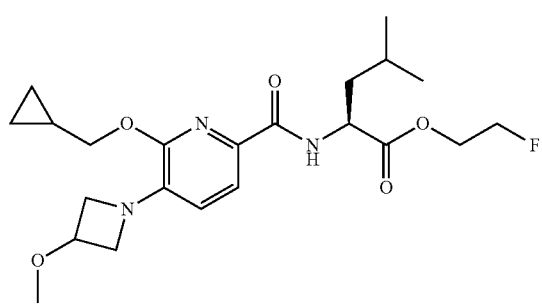 [SMILES: COC1CN(c2ccc(C(=O)N[C@@H](CC(C)C)C(=O)OCCF)nc2OCC2CC2)C1]

In analogy to the procedure described in example 1 b, (S)-2-(6-(cyclopropylmethoxy)-5-(3-methoxyazetidin-1-yl)picolinamido)-4-methylpentanoic acid (example 10 c) was reacted with fluoro-iodo-ethane to give the title compound as colorless oil, MS (ISP): 438.294 [MH$^+$].

Example 12

3-Fluoropropyl N-[6-(cyclopropylmethoxy)-5-(3-methoxyazetidin-1-yl)pyridine-2-carbonyl]-L-leucinate

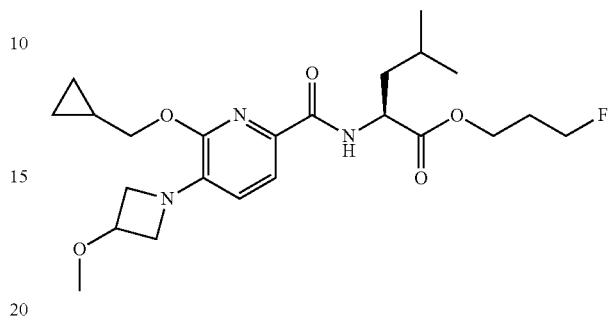

In analogy to the procedure described in example 1 b, (S)-2-(6-(cyclopropylmethoxy)-5-(3-methoxyazetidin-1-yl)picolinamido)-4-methylpentanoic acid (example 10 c) was reacted with 1-fluoro-3-iodopropane to give the title compound as colorless oil, MS (ISP): 452.351 [MH$^+$].

Example 13

Fluoromethyl N-[6-(cyclopropylmethoxy)-5-(pyrrolidin-1-yl)pyridine-2-carbonyl]-L-leucinate

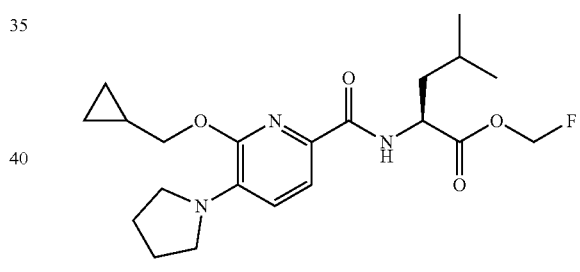

a) (S)-Methyl 2-(6-(cyclopropylmethoxy)-5-(pyrrolidin-1-yl)picolinamido)-4-methylpentanoate

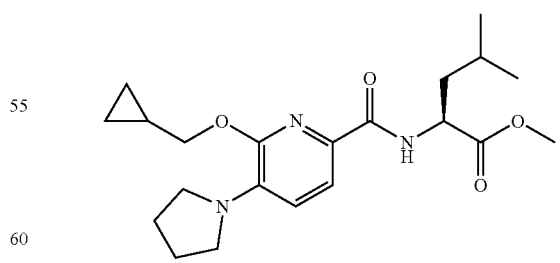

In analogy to the procedure described in example 10 b, (S)-methyl 2-(5-bromo-6-(cyclopropylmethoxy)picolinamido)-4-methylpentanoate (example 10 a) was reacted with pyrrolidine to give the title compound as light yellow oil, LC-MS (UV peak area/ESI) 95%, 390.2403 [MH$^+$].

b) (S)-2-(6-(Cyclopropylmethoxy)-5-(pyrrolidin-1-yl)picolinamido)-4-methylpentanoic acid

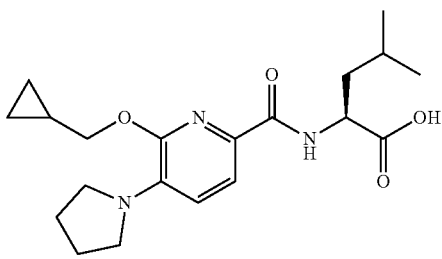 [SMILES: CC(C)C[C@H](NC(=O)c1ccc(N2CCCC2)c(OCC2CC2)n1)C(=O)O]

In analogy to the procedure described in example 10 c, (S)-methyl 2-(6-(cyclopropylmethoxy)-5-(pyrrolidin-1-yl)picolinamido)-4-methylpentanoate was hydrolyzed with KOH to give the title compound as brown oil which was used in the next reaction step without further purification, MS (ISP): 376.307 [MH$^+$].

c) Fluoromethyl N-[6-(cyclopropylmethoxy)-5-(pyrrolidin-1-yl)pyridine-2-carbonyl]-L-leucinate In analogy to the procedure described in example 1 b, (S)-2-(6-(cyclopropylmethoxy)-5-(pyrrolidin-1-yl)picolinamido)-4-methylpentanoic acid was reacted with fluoro-iodo-methane to give the title compound as light yellow oil, MS (ISP): 408.276 [MH$^+$].

Example 14

2-Fluoroethyl N-[6-(cyclopropylmethoxy)-5-(pyrrolidin-1-yl)pyridine-2-carbonyl]-L-leucinate

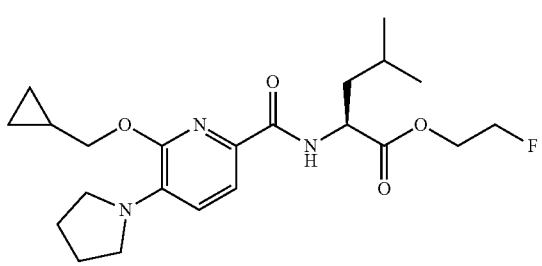 [SMILES: CC(C)C[C@H](NC(=O)c1ccc(N2CCCC2)c(OCC2CC2)n1)C(=O)OCCF]

In analogy to the procedure described in example 1 b, (S)-2-(6-(cyclopropylmethoxy)-5-(pyrrolidin-1-yl)picolinamido)-4-methylpentanoic acid (example 13 b) was reacted with fluoro-iodo-ethane to give the title compound as light brown oil, MS (ISP): 422.332 [MH$^+$].

Example 15

3-Fluoropropyl N-[6-(cyclopropylmethoxy)-5-(pyrrolidin-1-yl)pyridine-2-carbonyl]-L-leucinate

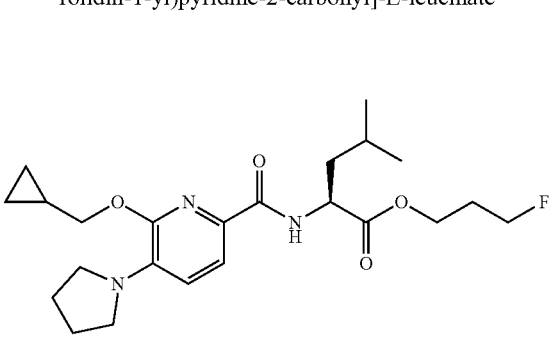

In analogy to the procedure described in example 1 b, (S)-2-(6-(cyclopropylmethoxy)-5-(pyrrolidin-1-yl)picolinamido)-4-methylpentanoic acid (example 13 b) was reacted with 1-fluoro-3-iodopropane to give the title compound as light brown oil, MS (ISP): 436.338 [MH$^+$].

Example 16

6-(Cyclopropylmethoxy)-N-[(2S)-1-(fluoromethoxy)-4-methylpentan-2-yl]-5-(pyrrolidin-1-yl)pyridine-2-carboxamide

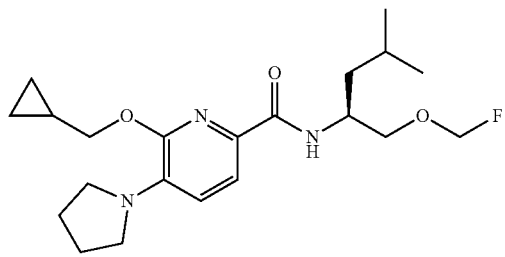 [SMILES: CC(C)C[C@@H](COCF)NC(=O)c1ccc(N2CCCC2)c(OCC2CC2)n1]

In a 5 mL round-bottomed flask, (S)-6-(cyclopropylmethoxy)-N-(1-hydroxy-4-methylpentan-2-yl)-5-(pyrrolidin-1-yl)picolinamide (CAN 1415894-55-1, 40 mg, 111 µmol, Eq: 1) was combined with DMF (1 mL) to give a colorless solution which was cooled to 0° C. Sodium hydride on mineral oil (22.1 mg, 553 µmol, Eq: 5) was added and stirring was continued for 30 min. Fluoro-iodo-methane (88.5 mg, 37.3 µL, 553 µmol, Eq: 5) was added, the mixture was allowed to warm to ambient temperature and stirring was continued for 1 h. The reaction mixture was diluted with EtOAc. The organic layers were combined and washed with sat. NaCl (3×25 mL). The organic layers were dried over Na$_2$SO$_4$ and concentrated in vacuo. The crude product was purified by column chromatography (SiO$_2$, 5 g, hept./EtOAc) to give the title compound (24 mg, 55%) as white solid, MS (ISP): 394.271 [MH$^+$].

Example 17

6-(Cyclopropylmethoxy)-N-[(2S)-1-(2-fluoroethoxy)-4-methylpentan-2-yl]-5-(pyrrolidin-1-yl)pyridine-2-carboxamide

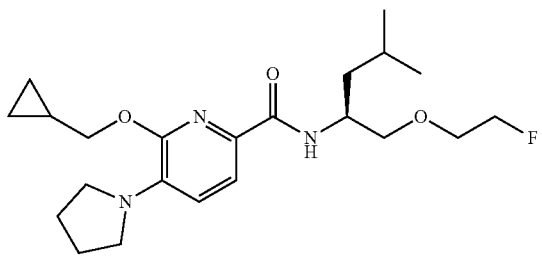 [SMILES: CC(C)C[C@@H](COCCF)NC(=O)c1ccc(N2CCCC2)c(OCC2CC2)n1]

In analogy to the procedure described in example 16, (S)-6-(cyclopropylmethoxy)-N-(1-hydroxy-4-methylpentan-2-yl)-5-(pyrrolidin-1-yl)picolinamide (CAN 1415894-55-1) was reacted with 1-fluoro-2-iodoethane to give the title compound as colorless oil, MS (ISP): 408.327 [MH$^+$].

Example 18

6-(Cyclopropylmethoxy)-N-[(2S)-1-(3-fluoropropoxy)-4-methylpentan-2-yl]-5-(pyrrolidin-1-yl)pyridine-2-carboxamide

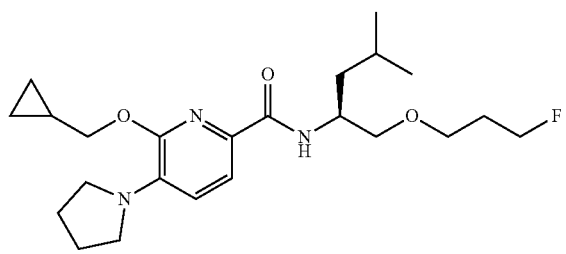 [SMILES: CC(C)C[C@@H](COCCCF)NC(=O)c1ccc(N2CCCC2)c(OCC2CC2)n1]

In analogy to the procedure described in example 16, (S)-6-(cyclopropylmethoxy)-N-(1-hydroxy-4-methylpentan-2-yl)-5-(pyrrolidin-1-yl)picolinamide (CAN 1415894-55-1) was reacted with 1-fluoro-3-fluoropropane to give the title compound as colorless oil, MS (ISP): 422.332 [MH$^+$].

Example 19

6-(Cylopropylmethoxy)-N-[(2S)-1-(fluoromethoxy)-3-methylbutan-2-yl]-5-(pyrrolidin-1-yl)pyridine-2-carboxamide

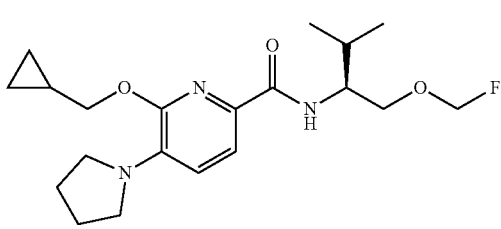 [SMILES: CC(C)[C@@H](COCF)NC(=O)c1ccc(N2CCCC2)c(OCC2CC2)n1]

a) (S)-6-(Cyclopropylmethoxy)-N-(1-hydroxy-3-methylbutan-2-yl)-5-(pyrrolidin-1-yl)picolinamide

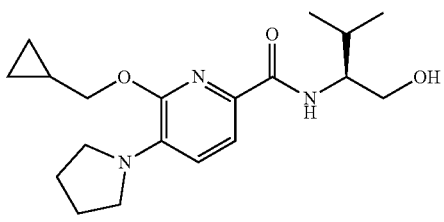 [SMILES: CC(C)[C@@H](CO)NC(=O)c1ccc(N2CCCC2)c(OCC2CC2)n1]

In a 50 mL round-bottomed flask, 6-(cyclopropylmethoxy)-5-(pyrrolidin-1-yl)picolinic acid (CAN 1415898-45-1, 295 mg, 1.12 mmol, Eq: 1) was combined with DMF (15 mL) to give a yellow solution. DIPEA (727 mg, 982 μL, 5.62 mmol, Eq: 5) and TBTU (397 mg, 1.24 mmol, Eq: 1.1) were added. L-Valinol (CAN 2026-48-4, 174 mg, 1.69 mmol, Eq: 1.5) was added and the mixture was stirred at ambient temperature for 1 h. EtOAc was added and the solution was washed with sat. NaHCO$_3$ (3×20 mL), 1 M HCl (3×20 mL), and sat. NaCl (3×20 mL). The organic layer was dried over Na$_2$SO$_4$ and concentrated in vacuo to give the title compound (240 mg, 61%) as light yellow oil which was used in the next step without further purification, MS (ISP): 348.239 [MH$^+$].

b) 6-(Cylopropylmethoxy)-N-[(2S)-1-(fluoromethoxy)-3-methylbutan-2-yl]-5-(pyrrolidin-1-yl)pyridine-2-carboxamide In analogy to the procedure described in example 16, (S)-6-(cyclopropylmethoxy)-N-(1-hydroxy-3-methylbutan-2-yl)-5-(pyrrolidin-1-yl)picolinamide was reacted with fluoro-iodo-methane to give the title compound as colorless oil, MS (ISP): 380.265 [MH$^+$].

Example 20

6-(Cyclopropylmethoxy)-N-[(2S)-1-(2-fluoroethoxy)-3-methylbutan-2-yl]-5-(pyrrolidin-1-yl)pyridine-2-carboxamide

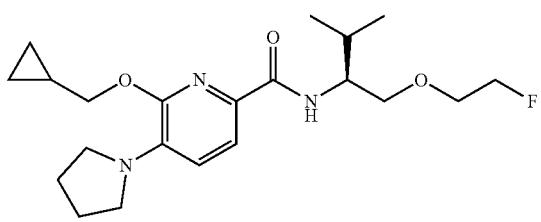 [SMILES: CC(C)[C@@H](COCCF)NC(=O)c1ccc(N2CCCC2)c(OCC2CC2)n1]

In analogy to the procedure described in example 16, (S)-6-(cyclopropylmethoxy)-N-(1-hydroxy-3-methylbutan-2-yl)-5-(pyrrolidin-1-yl)picolinamide (example 19 a) was reacted with 1-fluoro-2-iodoethane to give the title compound as colorless oil, MS (ISP): 394.326 [MH$^+$].

Example 21

6-(Cyclopropylmethoxy)-N-[(2S)-1-(3-fluoropropoxy)-3-methylbutan-2-yl]-5-(pyrrolidin-1-yl)pyridine-2-carboxamide

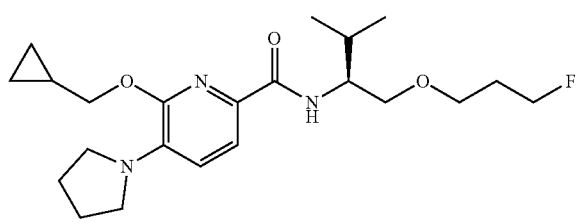 [SMILES: CC(C)[C@@H](COCCCF)NC(=O)c1ccc(N2CCCC2)c(OCC2CC2)n1]

In analogy to the procedure described in example 16, (S)-6-(cyclopropylmethoxy)-N-(1-hydroxy-3-methylbutan-2-yl)-5-(pyrrolidin-1-yl)picolinamide (example 19 a) was reacted with 1-iodo-3-fluoropropane to give the title compound as colorless oil, MS (ISP): 408.391 [MH$^+$].

Example 22

6-(Cyclopropylmethoxy)-N-[(2S)-1-(fluoromethoxy)propan-2-yl]-5-(pyrrolidin-1-yl)pyridine-2-carboxamide

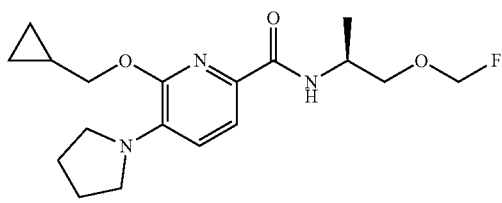 [SMILES: C[C@@H](COCF)NC(=O)c1ccc(N2CCCC2)c(OCC2CC2)n1]

a) (S)-6-(Cyclopropylmethoxy)-N-(1-hydroxypropan-2-yl)-5-(pyrrolidin-1-yl)picolinamide

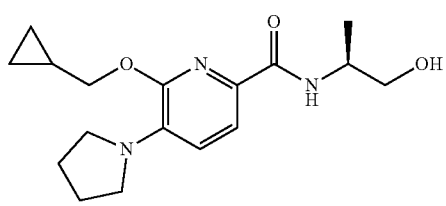 [SMILES: C[C@@H](CO)NC(=O)c1ccc(N2CCCC2)c(OCC2CC2)n1]

In analogy to the procedure described in example 19 a, 6-(cyclopropylmethoxy)-5-(pyrrolidin-1-yl)picolinic acid (CAN 1415898-45-1) was reacted with L-alaninol (CAN 2749-11-3) to give the title compound as light yellow oil, MS (ISP): 320.209 [MH$^+$].

b) 6-(Cyclopropylmethoxy)-N-[(2S)-1-(fluoromethoxy)propan-2-yl]-5-(pyrrolidin-1-yl)pyridine-2-carboxamide In analogy to the procedure described in example 16, (S)-6-(cyclopropylmethoxy)-N-(1-hydroxypropan-2-yl)-5-(pyrrolidin-1-yl)picolinamide was reacted with fluoro-iodomethane to give the title compound as colorless oil, MS (ISP): 352.204 [MH$^+$].

Example 23

6-(Cyclopropylmethoxy)-N-[(2S)-1-(2-fluoroethoxy)propan-2-yl]-5-(pyrrolidin-1-yl)pyridine-2-carboxamide

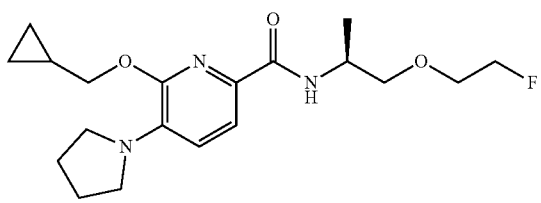 [SMILES: C[C@@H](COCCF)NC(=O)c1ccc(N2CCCC2)c(OCC2CC2)n1]

In analogy to the procedure described in example 16, (S)-6-(cyclopropylmethoxy)-N-(1-hydroxypropan-2-yl)-5-(pyrrolidin-1-yl)picolinamide (example 22 a) was reacted with 1-fluoro-2-iodoethane to give the title compound as colorless oil, MS (ISP): 366.298 [MH$^+$].

Example 24

6-(Cyclopropylmethoxy)-N-[(2S)-1-(3-fluoropropoxy)propan-2-yl]-5-(pyrrolidin-1-yl)pyridine-2-carboxamide

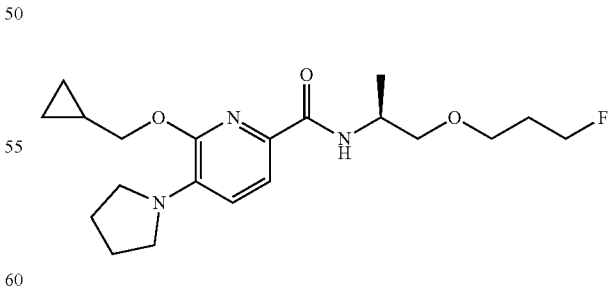

In analogy to the procedure described in example 16, (S)-6-(cyclopropylmethoxy)-N-(1-hydroxypropan-2-yl)-5-(pyrrolidin-1-yl)picolinamide (example 22 a) was reacted with 1-iodo-3-fluoropropane to give the title compound as colorless oil, MS (ISP): 380.265 [MH$^+$].

Example 25

6-(Cyclopropylmethoxy)-N-[(2S)-1-(fluoromethoxy)-4-methylpentan-2-yl]-5-(3-methoxyazetidin-1-yl)pyridine-2-carboxamide

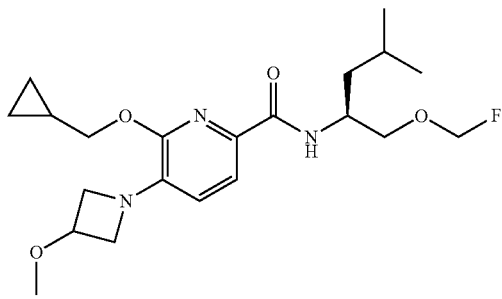 [SMILES: COC1CN(c2ccc(C(=O)N[C@H](COCF)CC(C)C)nc2OCC2CC2)C1]

a) (S)-6-(Cyclopropylmethoxy)-N-(1-hydroxy-4-methylpentan-2-yl)-5-(3-methoxyazetidin-1-yl)picolinamide

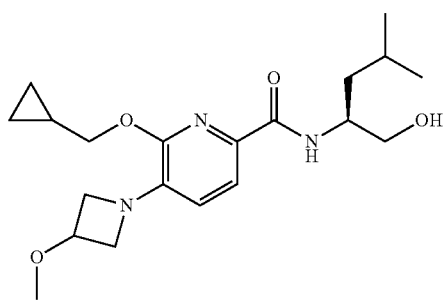 [SMILES: COC1CN(c2ccc(C(=O)N[C@H](CO)CC(C)C)nc2OCC2CC2)C1]

In analogy to the procedure described in example 19 a, 6-(cyclopropylmethoxy)-5-(3-methoxyazetidin-1-yl)picolinic acid (CAN 1613292-59-3) was condensed with L-leucinol (CAN 7533-40-6) to give the title compound as light yellow oil, MS (ISP): 378.309 [MH+].

b) 6-(Cyclopropylmethoxy)-N-[(2S)-1-(fluoromethoxy)-4-methylpentan-2-yl]-5-(3-methoxyazetidin-1-yl)pyridine-2-carboxamide In analogy to the procedure described in example 16, (S)-6-(cyclopropylmethoxy)-N-(1-hydroxy-4-methylpentan-2-yl)-5-(3-methoxyazetidin-1-yl)picolinamide was reacted with fluoro-iodo-methane to give the title compound as colorless oil, LC-MS (UV peak area/ESI) 100%, 380.265 [MH+].

Example 26

6-(Cyclopropylmethoxy)-5-(3,3-difluoroazetidin-1-yl)-N-[(2S)-1-(2-fluoroethoxy)-4-methylpentan-2-yl]pyridine-2-carboxamide

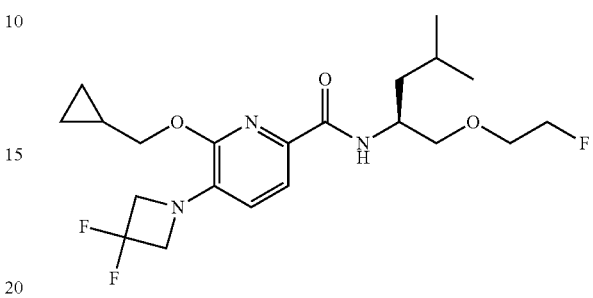

a) (S)-6-(Cyclopropylmethoxy)-5-(3,3-difluoroazetidin-1-yl)-N-(1-hydroxy-4-methylpentan-2-yl)picolinamide

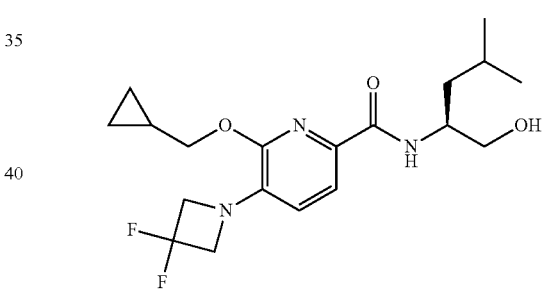

In analogy to the procedure described in example 19 a, 6-(cyclopropylmethoxy)-5-(3,3-difluoroazetidin-1-yl)picolinic acid (CAN 1415898-88-2) was condensed with L-leucinol (CAN 7533-40-6) to give the title compound as light yellow oil, MS (ISP): 384.279 [MH+].

b) 6-(Cyclopropylmethoxy)-5-(3,3-difluoroazetidin-1-yl)-N-[(2S)-1-(2-fluoroethoxy)-4-methylpentan-2-yl]pyridine-2-carboxamide In analogy to the procedure described in example 16, (S)-6-(cyclopropylmethoxy)-5-(3,3-difluoroazetidin-1-yl)-N-(1-hydroxy-4-methylpentan-2-yl)picolinamide was reacted with 1-fluoro-2-iodoethane to give the title compound as colorless oil, MS (ISP): 430.338. [MH+].

Example 27

6-(Cyclopropylmethoxy)-N-[(2S)-1-(2-fluoroethoxy)-4-methylpentan-2-yl]-5-(3-methoxyazetidin-1-yl)pyridine-2-carboxamide

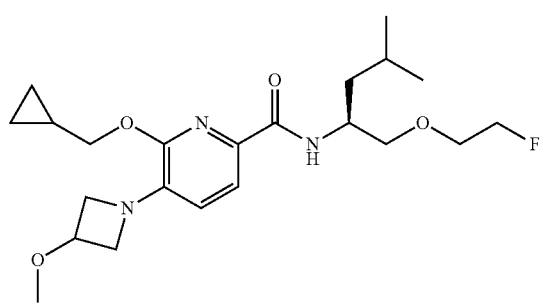 [SMILES: COC1CN(c2ccc(C(=O)N[C@H](COCCF)CC(C)C)nc2OCC2CC2)C1]

In analogy to the procedure described in example 16, (S)-6-(cyclopropylmethoxy)-N-(1-hydroxy-4-methylpentan-2-yl)-5-(3-methoxyazetidin-1-yl)picolinamide (example 25 a) was reacted with 1-fluoro-2-iodoethane to give the title compound as colorless oil, MS (ISP): 424.362 [MH$^+$].

Example 28

6-(Cyclopropylmethoxy)-N-[(2S)-1-(3-fluoropropoxy)-4-methylpentan-2-yl]-5-(3-methoxyazetidin-1-yl)pyridine-2-carboxamide

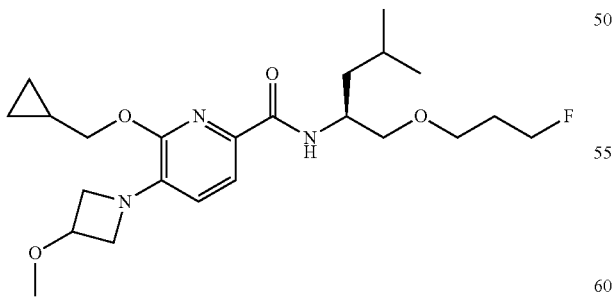

In analogy to the procedure described in example 16, (S)-6-(cyclopropylmethoxy)-N-(1-hydroxy-4-methylpentan-2-yl)-5-(3-methoxyazetidin-1-yl)picolinamide (example 25 a) was reacted with 1-iodo-3-fluoropropane to give the title compound as colorless oil, MS (ISP): 438.375 [MH$^+$].

Example 29

6-(Cyclopropylmethoxy)-N-[(2S)-1-(fluoromethoxy)-3-methylbutan-2-yl]-5-(3-methoxyazetidin-1-yl)pyridine-2-carboxamide

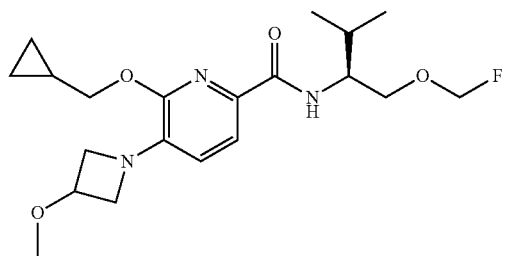 [SMILES: COC1CN(c2ccc(C(=O)N[C@H](COCF)C(C)C)nc2OCC2CC2)C1]

a) (S)-6-(Cyclopropylmethoxy)-N-(1-hydroxy-3-methylbutan-2-yl)-5-(3-methoxyazetidin-1-yl)picolinamide

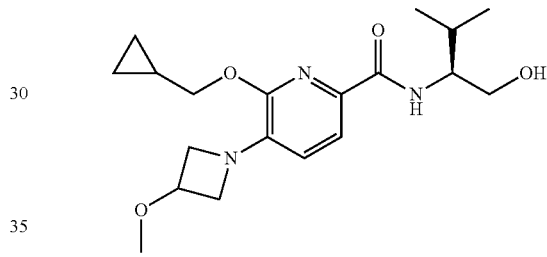

In analogy to the procedure described in example 19 a, 6-(cyclopropylmethoxy)-5-(3-methoxyazetidin-1-yl)picolinic acid (CAN 1613292-59-3) was condensed with L-valinol (CAN 2026-48-4) to give the title compound as light yellow oil, MS (ISP): 364.252 [MH$^+$].

b) 6-(Cyclopropylmethoxy)-N-[(2S)-1-(fluoromethoxy)-3-methylbutan-2-yl]-5-(3-methoxyazetidin-1-yl)pyridine-2-carboxamide In analogy to the procedure described in example 16, (S)-6-(cyclopropylmethoxy)-N-(1-hydroxy-3-methylbutan-2-yl)-5-(3-methoxyazetidin-1-yl)picolinamide was reacted with fluoro-iodo-methane to give the title compound as colorless oil, MS (ISP): 396.3 [MH$^+$].

Example 30

6-(Cyclopropylmethoxy)-N-[(2S)-1-(2-fluoroethoxy)-3-methylbutan-2-yl]-5-(3-methoxyazetidin-1-yl)pyridine-2-carboxamide

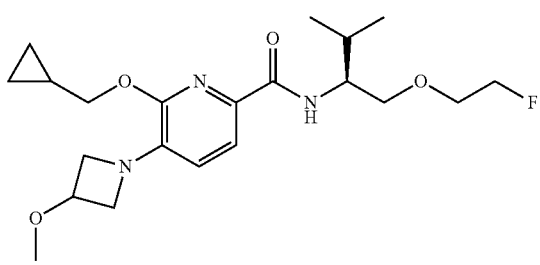 [SMILES: COC1CN(c2ccc(C(=O)N[C@H](COCCF)C(C)C)nc2OCC2CC2)C1]

In analogy to the procedure described in example 16, (S)-6-(cyclopropylmethoxy)-N-(1-hydroxy-3-methylbutan-2-yl)-5-(3-methoxyazetidin-1-yl)picolinamide (example 29 b) was reacted with 1-fluoro-2-iodoethane to give the title compound as colorless oil, MS (ISP): 410.335 [MH$^+$].

Example 31

6-(Cyclopropylmethoxy)-N-[(2S)-1-(3-fluoropropoxy)-3-methylbutan-2-yl]-5-(3-methoxyazetidin-1-yl)pyridine-2-carboxamide

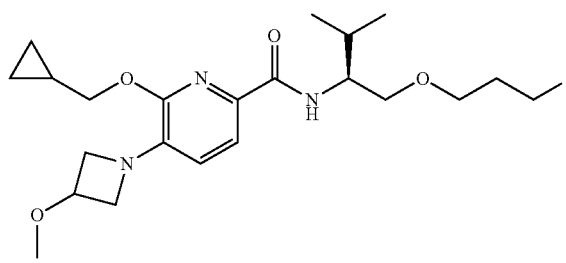

In analogy to the procedure described in example 16, (S)-6-(cyclopropylmethoxy)-N-(1-hydroxy-3-methylbutan-2-yl)-5-(3-methoxyazetidin-1-yl)picolinamide (example 29 b) was reacted with 1-iodo-3-fluoropropane to give the title compound as colorless oil, MS (ISP): 424.362 [MH$^+$].

Example 32

6-(Cyclopropylmethoxy)-N-[(2S)-1-(2-fluoroethoxy)propan-2-yl]-5-(3-methoxyazetidin-1-yl)pyridine-2-carboxamide

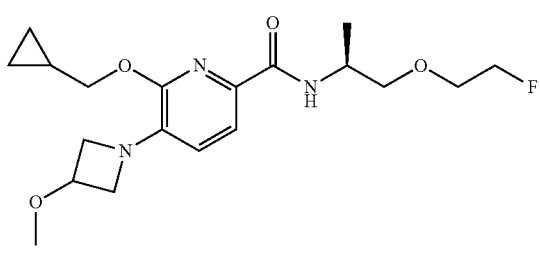 [SMILES: COC1CN(c2ccc(C(=O)N[C@@H](C)COCCF)nc2OCC2CC2)C1]

a) 6-(Cyclopropylmethoxy)-N-[(1S)-2-hydroxy-1-methyl-ethyl]-5-(3-methoxyazetidin-1-yl)pyridine-2-carboxamide

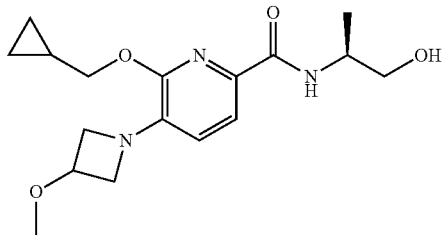 [SMILES: COC1CN(c2ccc(C(=O)N[C@@H](C)CO)nc2OCC2CC2)C1]

In analogy to the procedure described in example 19 a, 6-(cyclopropylmethoxy)-5-(3-methoxyazetidin-1-yl)picolinic acid (CAN 1613292-59-3) was condensed with L-alaninol (CAN 2749-11-3) to give the title compound as light yellow oil, MS (ISP): 336.242 [MH$^+$].

b) 6-(Cyclopropylmethoxy)-N-[(2S)-1-(2-fluoroethoxy)propan-2-yl]-5-(3-methoxyazetidin-1-yl)pyridine-2-carboxamide In analogy to the procedure described in example 16, 6-(cyclopropylmethoxy)-N-[(1S)-2-hydroxy-1-methyl-ethyl]-5-(3-methoxyazetidin-1-yl)pyridine-2-carboxamide was reacted with 1-fluoro-2-iodoethane to give the title compound as colorless oil, MS (ISP): 382.270 [MH$^+$].

Example 33

6-(Cyclopropylmethoxy)-N-[(2S)-1-(3-fluoropropoxy)propan-2-yl]-5-(3-methoxyazetidin-1-yl)pyridine-2-carboxamide

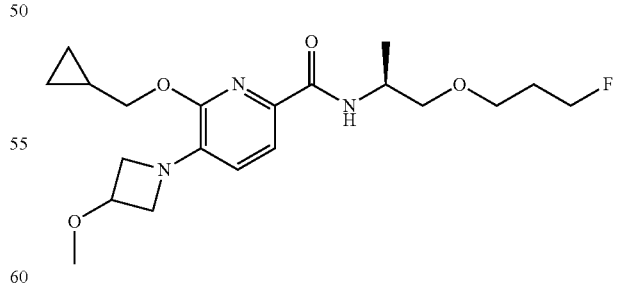

In analogy to the procedure described in example 16, 6-(cyclopropylmethoxy)-N-[(1S)-2-hydroxy-1-methyl-ethyl]-5-(3-methoxyazetidin-1-yl)pyridine-2-carboxamide (example 32 a) was reacted with 1-iodo-3-fluoropropane to give the title compound as colorless oil, MS (ISP): 396.279 [MH$^+$].

Example 34

6-(Cyclopropylmethoxy)-N-{3-[(fluoromethoxy)methyl]pentan-3-yl}-5-(3-methoxyazetidin-1-yl)pyridine-2-carboxamide

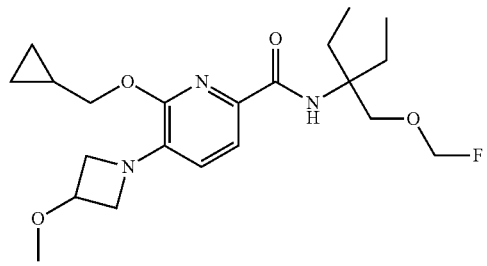 [SMILES: CCC(CC)(COCF)NC(=O)c1ccc(N2CC(OC)C2)c(OCC2CC2)n1]

a) 6-(Cyclopropylmethoxy)-N-(3-(hydroxymethyl)pentan-3-yl)-5-(3-methoxyazetidin-1-yl)picolinamide

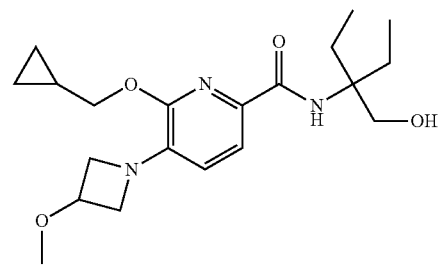 [SMILES: CCC(CC)(CO)NC(=O)c1ccc(N2CC(OC)C2)c(OCC2CC2)n1]

In analogy to the procedure described in example 19 a, 6-(cyclopropylmethoxy)-5-(3-methoxyazetidin-1-yl)picolinic acid (CAN 1613292-59-3) was condensed with 2-amino-2-ethylbutan-1-ol (CAN 19792-52-0) to give the title compound as light yellow oil, MS (ISP): 378.303 [MH$^+$].

b) 6-(Cyclopropylmethoxy)-N-{3-[(fluoromethoxy)methyl]pentan-3-yl}-5-(3-methoxyazetidin-1-yl)pyridine-2-carboxamide In analogy to the procedure described in example 16, 6-(cyclopropylmethoxy)-N-(3-(hydroxymethyl)pentan-3-yl)-5-(3-methoxyazetidin-1-yl)picolinamide was reacted with fluoro-iodo-methane to give the title compound as colorless oil, MS (ISP): 410.348 [MH$^+$].

Example 35

6-(Cyclopropylmethoxy)-N-{3-[(2-fluoroethoxy)methyl]pentan-3-yl}-5-(3-methoxyazetidin-1-yl)pyridine-2-carboxamide

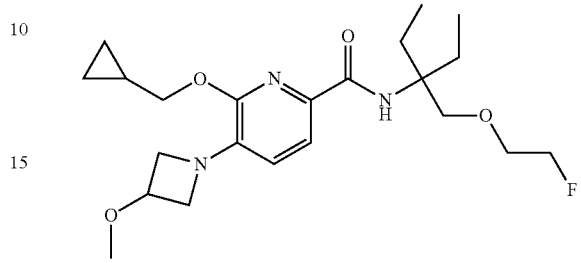

In analogy to the procedure described in example 16, 6-(cyclopropylmethoxy)-N-(3-(hydroxymethyl)pentan-3-yl)-5-(3-methoxyazetidin-1-yl)picolinamide (example 34 a) was reacted with 1-fluoro-2-iodoethane to give the title compound as light brown oil, MS (ISP): 424.362 [MH$^+$].

Example 36

6-(Cyclopropylmethoxy)-N-{3-[(3-fluoropropoxy)methyl]pentan-3-yl}-5-(3-methoxyazetidin-1-yl)pyridine-2-carboxamide

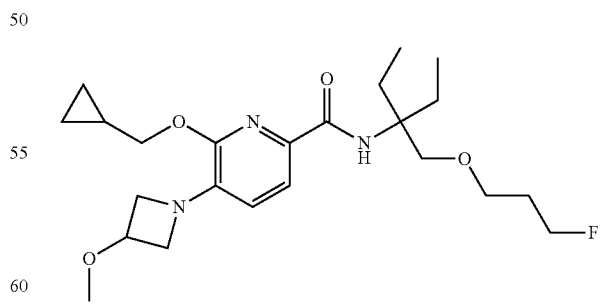

In analogy to the procedure described in example 16, 6-(cyclopropylmethoxy)-N-(3-(hydroxymethyl)pentan-3-yl)-5-(3-methoxyazetidin-1-yl)picolinamide (example 34 a) was reacted with 1-iodo-3-fluoropropane to give the title compound as light brown oil, MS (ISP): 438.346 [MH$^+$].

Example 37

6-(Cyclopropylmethoxy)-N-[(2R)-1-(2-fluoroethoxy)-4-methylpentan-2-yl]-5-(pyrrolidin-1-yl)pyridine-2-carboxamide

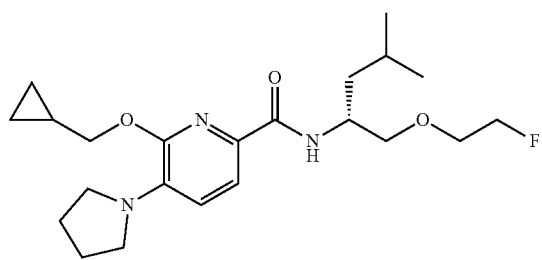 [SMILES: CC(C)C[C@H](COCCF)NC(=O)c1ccc(N2CCCC2)c(OCC2CC2)n1]

a) (R)-6-(Cyclopropylmethoxy)-N-(1-hydroxy-4-methylpentan-2-yl)-5-(pyrrolidin-1-yl)picolinamide

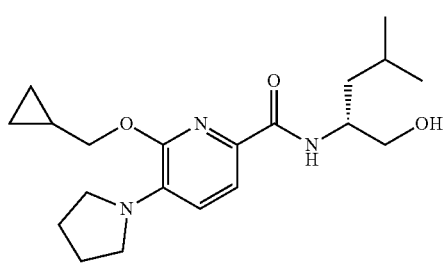 [SMILES: CC(C)C[C@H](CO)NC(=O)c1ccc(N2CCCC2)c(OCC2CC2)n1]

In analogy to the procedure described in example 19 a, 6-(cyclopropylmethoxy)-5-(pyrrolidin-1-yl)picolinic acid (CAN 1415898-45-1) was condensed with D-leucinol (CAN 53448-09-2) to give the title compound as colorless oil, MS (ISP): 362.725. [MH$^+$].

b) 6-(Cyclopropylmethoxy)-N-[(2R)-1-(2-fluoroethoxy)-4-methylpentan-2-yl]-5-(pyrrolidin-1-yl)pyridine-2-carboxamide In analogy to the procedure described in example 16, (R)-6-(cyclopropylmethoxy)-N-(1-hydroxy-4-methylpentan-2-yl)-5-(pyrrolidin-1-yl)picolinamide was reacted with 1-fluoro-2-iodoethane to give the title compound as colorless oil, MS (ISP): 408.359 [MH$^+$].

Example 38

6-(Cyclopropylmethoxy)-N-[(2R)-1-(2-fluoroethoxy)-4-methylpentan-2-yl]-5-(3-methoxyazetidin-1-yl)pyridine-2-carboxamide

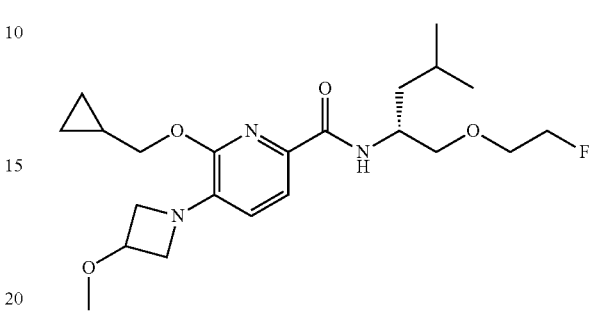

a) (R)-6-(Cyclopropylmethoxy)-N-(1-hydroxy-4-methylpentan-2-yl)-5-(3-methoxyazetidin-1-yl)picolinamide

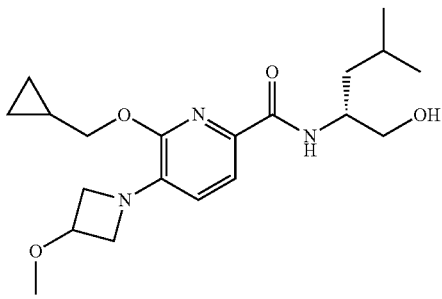 [SMILES: COC1CN(c2ccc(C(=O)N[C@@H](CO)CC(C)C)nc2OCC2CC2)C1]

In analogy to the procedure described in example 19 a, 6-(cyclopropylmethoxy)-5-(3-methoxyazetidin-1-yl)picolinic acid (CAN 1613292-59-3) was condensed with D-leucinol (CAN 53448-09-2) to give the title compound as light yellow oil, MS (ISP): 378.3 [MH$^+$].

b) 6-(Cyclopropylmethoxy)-N-[(2R)-1-(2-fluoroethoxy)-4-methylpentan-2-yl]-5-(3-methoxyazetidin-1-yl)pyridine-2-carboxamide In analogy to the procedure described in example 16, (R)-6-(cyclopropylmethoxy)-N-(1-hydroxy-4-methylpentan-2-yl)-5-(3-methoxyazetidin-1-yl)picolinamide was reacted with 1-fluoro-2-iodoethane to give the title compound as colorless oil, MS (ISP): 424.327 [MH$^+$].

Example 39

6-(Cyclopropylmethoxy)-5-(3-fluoro-3-methylazetidin-1-yl)-N-(3-(3-fluoropropylcarbamoyl)pentan-3-yl)picolinamide

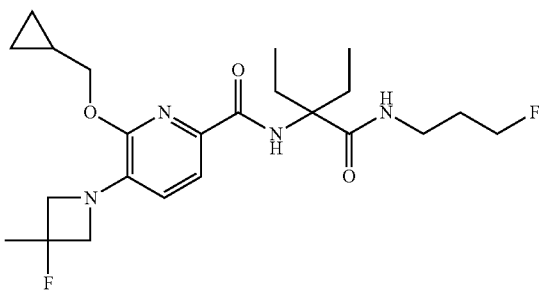 [SMILES: CCC(CC)(NC(=O)c1ccc(N2CC(C)(F)C2)c(OCC2CC2)n1)C(=O)NCCCF]

In a 5 mL pear-shaped flask, 6-(cyclopropylmethoxy)-5-(3-fluoro-3-methylazetidin-1-yl)picolinic acid (CAN 1812888-92-8, 5 mg, 17.8 µmol, Eq: 1.0), 2-amino-2-ethyl-N-(3-fluoropropyl)butanamide hydrochloride (CAN 1613239-88-5, 4.45 mg, 19.6 µmol, Eq: 1.10), 2-bromo-1-ethylpyridinium tetrafluoroborate (5.37 mg, 19.6 µmol, Eq: 1.10) and DIPEA (8.07 mg, 10.7 µL, 62.4 µmol, Eq: 3.50) were combined with 1,4-dioxane (100 µL) to give a light yellow solution. The reaction mixture was stirred for 16 h at ambient temperature and brought to dryness. The crude was purified by preparative TLC (silica gel, EtOAc, elution with $CH_2Cl_2$/EtOAc 1:1) to give the title compound (5 mg, 62%) as white solid, MS (ESI): 453.3 [MH$^+$].

Example 40

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM MgCl2, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor.

The compounds according to formula (I) have an activity in the above assay (Ki) between 0.5 nM and 10 µM. Particular compounds of formula (I) have an activity in the above assay (Ki) between 0.5 nM and 3 µM. Other particular compounds of formula (I) have an activity in the above assay (Ki) between 0.5 nM and 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1x HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of cannabinoid agonists generated from this assay for reference compounds were in agreement with the values published in the scientific literature.

In the foregoing assay, the compounds according to the invention have a human CB2 $EC_{50}$ which is between 0.5 nM and 10 µM. Particular compounds according to the invention have a human CB2 $EC_{50}$ between 0.5 nM and 1 µM. Further particular compounds according to the invention have a human CB2 $EC_{50}$ between 0.5 nM and 100 nM. They exhibit at least 10 fold selectivity against the human CB1 receptor in, either both of the radioligand and cAMP assay, or in one of these two assays.

Results obtained for representative compounds of the invention are given in the following table.

| Example | Binding assay human CB2 Ki [µM] |
|---|---|
| 1 | 0.002 |
| 2 | 0.002 |
| 3 | 0.006 |
| 4 | 0.006 |
| 5 | 0.007 |
| 6 | 0.019 |
| 7 | 0.005 |
| 8 | 0.002 |
| 9 | 0.003 |
| 10 | 0.336 |
| 11 | 0.015 |
| 12 | 0.046 |
| 13 | 0.063 |
| 14 | 0.015 |
| 15 | 0.04 |
| 16 | 0.008 |
| 17 | 0.01 |
| 18 | 0.04 |
| 19 | 0.07 |

-continued

| Example | Binding assay human CB2 Ki [μM] |
|---|---|
| 20 | 0.06 |
| 21 | 0.156 |
| 22 | 0.787 |
| 23 | 0.49 |
| 24 | 0.671 |
| 25 | 0.014 |
| 26 | 0.024 |
| 27 | 0.018 |
| 28 | 0.031 |
| 29 | 0.269 |
| 30 | 0.165 |
| 31 | 0.247 |
| 32 | 3.118 |
| 33 | 2.81 |
| 34 | 0.033 |
| 35 | 0.062 |
| 36 | 0.068 |
| 37 | 0.288 |
| 38 | 1.303 |
| 39 | 0.524 |

The invention claimed is:

1. A compound of formula (I):

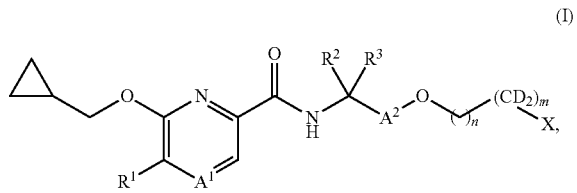

or a pharmaceutically acceptable salt thereof,
wherein
$R^1$ is alkoxyazetidinyl, dihaloazetidinyl or pyrrolidinyl;
$R^2$ and $R^3$ are independently selected from hydrogen and alkyl;
$A^1$ is —CH— or nitrogen;
$A^2$ is —CH$_2$— or carbonyl;
X is halogen;
n is 0 to 3; and
m is 0 or 1;
provided that m and n are not both 0 at the same time.

2. The compound of claim 1, wherein $R^1$ is methoxyazetidinyl, difluoroazetidinyl or pyrrolidinyl.

3. The compound of claim 1, wherein $R^2$ and $R^3$ are independently selected from hydrogen, ethyl and butyl.

4. The compound of claim 3, wherein $R^2$ and $R^3$ are both ethyl at the same time, or one of $R^2$ and $R^3$ is hydrogen and the other one is butyl.

5. The compound of claim 1, wherein $A^1$ is —CH—.

6. The compound of claim 1, wherein X is fluorine.

7. The compound of claim 1, wherein n is 1, 2 or 3.

8. The compound of claim 1 selected from the group consisting of:
fluoromethyl 2-{[6-(cyclopropylmethoxy)-5-(3-methoxyazetidin-1-yl)pyridine-2-carbonyl]amino}-2-ethylbutanoate;
2-fluoroethyl 2-{[6-(cyclopropylmethoxy)-5-(3-methoxyazetidin-1-yl)pyridine-2-carbonyl]amino}-2-ethylbutanoate;
3-fluoropropyl 2-{[6-(cyclopropylmethoxy)-5-(3-methoxyazetidin-1-yl)pyridine-2-carbonyl]amino}-2-ethylbutanoate;
fluoromethyl 2-{[6-(cyclopropylmethoxy)-5-(3,3-difluoroazetidin-1-yl)pyridine-2-carbonyl]amino}-2-ethylbutanoate;
2-fluoroethyl 2-{[6-(cyclopropylmethoxy)-5-(3,3-difluoroazetidin-1-yl)pyridine-2-carbonyl]amino}-2-ethylbutanoate;
3-fluoropropyl 2-{[6-(cyclopropylmethoxy)-5-(3,3-difluoroazetidin-1-yl)pyridine-2-carbonyl]amino}-2-ethylbutanoate;
3-fluoropropyl 2-{[6-(cyclopropylmethoxy)-5-(pyrrolidin-1-yl)pyridine-2-carbonyl]amino}-2-ethylbutanoate;
fluoromethyl 2-{[6-(cyclopropylmethoxy)-5-(pyrrolidin-1-yl)pyridine-2-carbonyl]amino}-2-ethylbutanoate;
2-fluoroethyl 2-{[6-(cyclopropylmethoxy)-5-(pyrrolidin-1-yl)pyridine-2-carbonyl]amino}-2-ethylbutanoate;
fluoromethyl N-[6-(cyclopropylmethoxy)-5-(3-methoxyazetidin-1-yl)pyridine-2-carbonyl]-L-leucinate;
2-fluoroethyl N-[6-(cyclopropylmethoxy)-5-(3-methoxyazetidin-1-yl)pyridine-2-carbonyl]-L-leucinate;
3-fluoropropyl N-[6-(cyclopropylmethoxy)-5-(3-methoxyazetidin-1-yl)pyridine-2-carbonyl]-L-leucinate;
fluoromethyl N-[6-(cyclopropylmethoxy)-5-(pyrrolidin-1-yl)pyridine-2-carbonyl]-L-leucinate;
2-fluoroethyl N-[6-(cyclopropylmethoxy)-5-(pyrrolidin-1-yl)pyridine-2-carbonyl]-L-leucinate;
3-fluoropropyl N-[6-(cyclopropylmethoxy)-5-(pyrrolidin-1-yl)pyridine-2-carbonyl]-L-leucinate;
6-(cyclopropylmethoxy)-N-[(2S)-1-(fluoromethoxy)-4-methylpentan-2-yl]-5-(pyrrolidin-1-yl)pyridine-2-carboxamide;
6-(cyclopropylmethoxy)-N-[(2R)-1-(2-fluoroethoxy)-4-methylpentan-2-yl]-5-(pyrrolidin-1-yl)pyridine-2-carboxamide;
6-(cyclopropylmethoxy)-N-[(2S)-1-(2-fluoroethoxy)-4-methylpentan-2-yl]-5-(pyrrolidin-1-yl)pyridine-2-carboxamide;
6-(cyclopropylmethoxy)-N-[(2S)-1-(3-fluoropropoxy)-4-methylpentan-2-yl]-5-(pyrrolidin-1-yl)pyridine-2-carboxamide;
6-(cyclopropylmethoxy)-N-[(2S)-1-(fluoromethoxy)-3-methylbutan-2-yl]-5-(pyrrolidin-1-yl)pyridine-2-carboxamide;
6-(cyclopropylmethoxy)-N-[(2S)-1-(2-fluoroethoxy)-3-methylbutan-2-yl]-5-(pyrrolidin-1-yl)pyridine-2-carboxamide;
6-(cyclopropylmethoxy)-N-[(2S)-1-(3-fluoropropoxy)-3-methylbutan-2-yl]-5-(pyrrolidin-1-yl)pyridine-2-carboxamide;
6-(cyclopropylmethoxy)-N-[(2S)-1-(fluoromethoxy)propan-2-yl]-5-(pyrrolidin-1-yl)pyridine-2-carboxamide;
6-(cyclopropylmethoxy)-N-[(2S)-1-(2-fluoroethoxy)propan-2-yl]-5-(pyrrolidin-1-yl)pyridine-2-carboxamide;
6-(cyclopropylmethoxy)-N-[(2S)-1-(3-fluoropropoxy)propan-2-yl]-5-(pyrrolidin-1-yl)pyridine-2-carboxamide;
6-(cyclopropylmethoxy)-N-[(2S)-1-(fluoromethoxy)-4-methylpentan-2-yl]-5-(3-methoxyazetidin-1-yl)pyridine-2-carboxamide;
6-(cyclopropylmethoxy)-5-(3,3-difluoroazetidin-1-yl)-N-[(2S)-1-(2-fluoroethoxy)-4-methylpentan-2-yl]pyridine-2-carboxamide;

6-(cyclopropylmethoxy)-N-[(2R)-1-(2-fluoroethoxy)-4-methylpentan-2-yl]-5-(3-methoxyazetidin-1-yl)pyridine-2-carboxamide;

6-(cyclopropylmethoxy)-N-[(2S)-1-(2-fluoroethoxy)-4-methylpentan-2-yl]-5-(3-methoxyazetidin-1-yl)pyridine-2-carboxamide;

6-(cyclopropylmethoxy)-N-[(2S)-1-(3-fluoropropoxy)-4-methylpentan-2-yl]-5-(3-methoxyazetidin-1-yl)pyridine-2-carboxamide;

6-(cyclopropylmethoxy)-N-[(2S)-1-(fluoromethoxy)-3-methylbutan-2-yl]-5-(3-methoxyazetidin-1-yl)pyridine-2-carboxamide;

6-(cyclopropylmethoxy)-N-[(2S)-1-(2-fluoroethoxy)-3-methylbutan-2-yl]-5-(3-methoxyazetidin-1-yl)pyridine-2-carboxamide;

6-(cyclopropylmethoxy)-N-[(2S)-1-(3-fluoropropoxy)-3-methylbutan-2-yl]-5-(3-methoxyazetidin-1-yl)pyridine-2-carboxamide;

6-(cyclopropylmethoxy)-N-[(2S)-1-(2-fluoroethoxy)propan-2-yl]-5-(3-methoxyazetidin-1-yl)pyridine-2-carboxamide;

6-(cyclopropylmethoxy)-N-[(2S)-1-(3-fluoropropoxy)propan-2-yl]-5-(3-methoxyazetidin-1-yl)pyridine-2-carboxamide;

6-(cyclopropylmethoxy)-N-{3-[(fluoromethoxy)methyl]pentan-3-yl}-5-(pyrrolidin-1-yl)pyridine-2-carboxamide;

6-(cyclopropylmethoxy)-N-{3-[(2-fluoroethoxy)methyl]pentan-3-yl}-5-(pyrrolidin-1-yl)pyridine-2-carboxamide;

6-(cyclopropylmethoxy)-N-{3-[(3-fluoropropoxy)methyl]pentan-3-yl}-5-(pyrrolidin-1-yl)pyridine-2-carboxamide;

6-(cyclopropylmethoxy)-N-{3-[(fluoromethoxy)methyl]pentan-3-yl}-5-(3-methoxyazetidin-1-yl)pyridine-2-carboxamide;

6-(cyclopropylmethoxy)-N-{3-[(2-fluoroethoxy)methyl]pentan-3-yl}-5-(3-methoxyazetidin-1-yl)pyridine-2-carboxamide;

6-(cyclopropylmethoxy)-N-{3-[(3-fluoropropoxy)methyl]pentan-3-yl}-5-(3-methoxyazetidin-1-yl)pyridine-2-carboxamide;

fluoromethyl 2-{[6-(cyclopropylmethoxy)-5-(3-methoxyazetidin-1-yl)pyrazine-2-carbonyl]amino}-2-ethylbutanoate;

2-fluoroethyl 2-{[6-(cyclopropylmethoxy)-5-(3-methoxyazetidin-1-yl)pyrazine-2-carbonyl]amino}-2-ethylbutanoate;

3-fluoropropyl 2-{[6-(cyclopropylmethoxy)-5-(3-methoxyazetidin-1-yl)pyrazine-2-carbonyl]amino}-2-ethylbutanoate;

fluoro(dideuterio)methyl 2-{[6-(cyclopropylmethoxy)-5-(3-methoxyazetidin-1-yl)pyridine-2-carbonyl]amino}-2-ethylbutanoate;

2-fluoro(2,2-dideuterio)ethyl 2-{[6-(cyclopropylmethoxy)-5-(3-methoxyazetidin-1-yl)pyridine-2-carbonyl]amino}-2-ethylbutanoate;

3-fluoro(3,3-dideuterio)propyl 2-{[6-(cyclopropylmethoxy)-5-(3-methoxyazetidin-1-yl)pyridine-2-carbonyl]amino}-2-ethylbutanoate;

fluoro(dideuterio)methyl 2-{[6-(cyclopropylmethoxy)-5-(3,3-difluoroazetidin-1-yl)pyridine-2-carbonyl]amino}-2-ethylbutanoate;

2-fluoro(2,2-dideuterio)ethyl 2-{[6-(cyclopropylmethoxy)-5-(3,3-difluoroazetidin-1-yl)pyridine-2-carbonyl]amino}-2-ethylbutanoate;

3-fluoro(3,3-dideuterio)propyl 2-{[6-(cyclopropylmethoxy)-5-(3,3-difluoroazetidin-1-yl)pyridine-2-carbonyl]amino}-2-ethylbutanoate;

3-fluoro(3,3-dideuterio)propyl 2-{[6-(cyclopropylmethoxy)-5-(pyrrolidin-1-yl)pyridine-2-carbonyl]amino}-2-ethylbutanoate;

fluoro(dideuterio)methyl 2-{[6-(cyclopropylmethoxy)-5-(pyrrolidin-1-yl)pyridine-2-carbonyl]amino}-2-ethylbutanoate;

2-fluoro(2,2-dideuterio)ethyl 2-{[6-(cyclopropylmethoxy)-5-(pyrrolidin-1-yl)pyridine-2-carbonyl]amino}-2-ethylbutanoate;

6-(cyclopropylmethoxy)-N-[(2S)-1-{[fluoro(dideuterio)methyl]oxy}-4-methylpentan-2-yl]-5-(pyrrolidin-1-yl)pyridine-2-carboxamide;

6-(cyclopropylmethoxy)-N-[(2S)-1-{[2-fluoro(2,2-dideuterio)ethyl]oxy}-4-methylpentan-2-yl]-5-(pyrrolidin-1-yl)pyridine-2-carboxamide;

6-(cyclopropylmethoxy)-N-[(2S)-1-{[3-fluoro(3,3-dideuterio)propyl]oxy}-4-methylpentan-2-yl]-5-(pyrrolidin-1-yl)pyridine-2-carboxamide;

6-(cyclopropylmethoxy)-N-[(2S)-1-{[fluoro(dideuterio)methyl]oxy}-3-methylbutan-2-yl]-5-(pyrrolidin-1-yl)pyridine-2-carboxamide;

6-(cyclopropylmethoxy)-N-[(2S)-1-{[2-fluoro(2,2-dideuterio)ethyl]oxy}-3-methylbutan-2-yl]-5-(pyrrolidin-1-yl)pyridine-2-carboxamide;

6-(cyclopropylmethoxy)-N-[(2S)-1-{[3-fluoro(3,3-dideuterio)propyl]oxy}-3-methylbutan-2-yl]-5-(pyrrolidin-1-yl)pyridine-2-carboxamide;

6-(cyclopropylmethoxy)-N-[(2S)-1-{[fluoro(dideuterio)methyl]oxy}propan-2-yl]-5-(pyrrolidin-1-yl)pyridine-2-carboxamide;

6-(cyclopropylmethoxy)-N-[(2S)-1-{[2-fluoro(2,2-dideuterio)ethyl]oxy}propan-2-yl]-5-(pyrrolidin-1-yl)pyridine-2-carboxamide;

6-(cyclopropylmethoxy)-N-[(2S)-1-{[3-fluoro(3,3-dideuterio)propyl]oxy}propan-2-yl]-5-(pyrrolidin-1-yl)pyridine-2-carboxamide;

6-(cyclopropylmethoxy)-N-[(2S)-1-{[fluoro(dideuterio)methyl]oxy}-4-methylpentan-2-yl]-5-(3-methoxyazetidin-1-yl)pyridine-2-carboxamide;

6-(cyclopropylmethoxy)-N-[(2S)-1-{[2-fluoro(2,2-dideuterio)ethyl]oxy}-4-methylpentan-2-yl]-5-(3-methoxyazetidin-1-yl)pyridine-2-carboxamide;

6-(cyclopropylmethoxy)-N-[(2S)-1-{[3-fluoro(3,3-dideuterio)propyl]oxy}-4-methylpentan-2-yl]-5-(3-methoxyazetidin-1-yl)pyridine-2-carboxamide;

6-(cyclopropylmethoxy)-N-[(2S)-1-{[fluoro(dideuterio)methyl]oxy}-3-methylbutan-2-yl]-5-(3-methoxyazetidin-1-yl)pyridine-2-carboxamide;

6-(cyclopropylmethoxy)-N-[(2S)-1-{[2-fluoro(2,2-dideuterio)ethyl]oxy}-3-methylbutan-2-yl]-5-(3-methoxyazetidin-1-yl)pyridine-2-carboxamide;

6-(cyclopropylmethoxy)-N-[(2S)-1-{[3-fluoro(3,3-dideuterio)propyl]oxy}-3-methylbutan-2-yl]-5-(3-methoxyazetidin-1-yl)pyridine-2-carboxamide;

6-(cyclopropylmethoxy)-N-[(2S)-1-{[2-fluoro(2,2-dideuterio)ethyl]oxy}propan-2-yl]-5-(3-methoxyazetidin-1-yl)pyridine-2-carboxamide;

6-(cyclopropylmethoxy)-N-[(2S)-1-{[3-fluoro(3,3-dideuterio)propyl]oxy}propan-2-yl]-5-(3-methoxyazetidin-1-yl)pyridine-2-carboxamide;

6-(cyclopropylmethoxy)-N-[3-({[fluoro(dideuterio)methyl]oxy}methyl)pentan-3-yl]-5-(pyrrolidin-1-yl)pyridine-2-carboxamide;

6-(cyclopropylmethoxy)-N-[3-({[2-fluoro(2,2-dideuterio)ethyl]oxy}methyl)pentan-3-yl]-5-(pyrrolidin-1-yl)pyridine-2-carboxamide;

6-(cyclopropylmethoxy)-N-[3-({[3-fluoro(3,3-dideuterio)propyl]oxy}methyl)pentan-3-yl]-5-(pyrrolidin-1-yl)pyridine-2-carboxamide;

6-(cyclopropylmethoxy)-N-[3-({[fluoro(dideuterio)methyl]oxy}methyl)pentan-3-yl]-5-(3-methoxyazetidin-1-yl)pyridine-2-carboxamide;

6-(cyclopropylmethoxy)-N-[3-({[2-fluoro(2,2-dideuterio)ethyl]oxy}methyl)pentan-3-yl]-5-(3-methoxyazetidin-1-yl)pyridine-2-carboxamide;

6-(cyclopropylmethoxy)-N-[3-({[3-fluoro(3,3-dideuterio)propyl]oxy}methyl)pentan-3-yl]-5-(3-methoxyazetidin-1-yl)pyridine-2-carboxamide;

ethyl 2-{[6-(cyclopropylmethoxy)-5-(3-methoxyazetidin-1-yl)pyridine-2-carbonyl]amino}-2-ethyl-4-fluoro(4,4-dideuterio)butanoate;

ethyl 2-{[6-(cyclopropylmethoxy)-5-(3-methoxyazetidin-1-yl)pyridine-2-carbonyl]amino}-2-ethyl-4-fluoro(4,4-dideuterio)butanoate;

6-(cyclopropylmethoxy)-5-(3-fluoro-3-methylazetidin-1-yl)-N-(3-(3-fluoropropylcarbamoyl)pentan-3-yl)picolinamide;

ethyl 2-{[6-(cyclopropylmethoxy)-5-(3-methoxyazetidin-1-yl)pyridine-2-carbonyl]amino}-2-ethyl-4-fluorobutanoate;

ethyl 2-{[6-(cyclopropylmethoxy)-5-(3-methoxyazetidin-1-yl)pyridine-2-carbonyl]amino}-2-ethyl-3-fluorobutanoate;

ethyl 2-{[6-(cyclopropylmethoxy)-5-(3-methoxyazetidin-1-yl)pyridine-2-carbonyl]amino}-2-ethyl-4-fluorobutanoate; and ethyl 2-{[6-(cyclopropylmethoxy)-5-(3-methoxyazetidin-1-yl)pyridine-2-carbonyl]amino}-2-ethyl-3-fluorobutanoate;

or a pharmaceutically acceptable salt thereof.

9. The compound of claim 1 selected from the group consisting of:

2-fluoroethyl 2-{[6-(cyclopropylmethoxy)-5-(3-methoxyazetidin-1-yl)pyridine-2-carbonyl]amino}-2-ethyl butanoate;

3-fluoropropyl 2-{[6-(cyclopropylmethoxy)-5-(3-methoxyazetidin-1-yl)pyridine-2-carbonyl]amino}-2-ethylbutanoate;

2-fluoroethyl N-[6-(cyclopropylmethoxy)-5-(3-methoxyazetidin-1-yl)pyridine-2-carbonyl]-L-leucinate;

2-fluoroethyl N-[6-(cyclopropylmethoxy)-5-(pyrrolidin-1-yl)pyridine-2-carbonyl]-L-leucinate;

6-(cyclopropylmethoxy)-N-[(2S)-1-(fluoromethoxy)-4-methylpentan-2-yl]-5-(pyrrolidin-1-yl)pyridine-2-carboxamide;

6-(cyclopropylmethoxy)-N-[(2S)-1-(2-fluoroethoxy)-4-methylpentan-2-yl]-5-(pyrrolidin-1-yl)pyridine-2-carboxamide;

6-(cyclopropylmethoxy)-N-[(2S)-1-(fluoromethoxy)-4-methylpentan-2-yl]-5-(3-methoxyazetidin-1-yl)pyridine-2-carboxamide;

6-(cyclopropylmethoxy)-5-(3,3-difluoroazetidin-1-yl)-N-[(2S)-1-(2-fluoroethoxy)-4-methylpentan-2-yl]pyridine-2-carboxamide; and 6-(cyclopropylmethoxy)-N-[(2S)-1-(2-fluoroethoxy)-4-methylpentan-2-yl]-5-(3-methoxyazetidin-1-yl)pyridine-2-carboxamide;

or a pharmaceutically acceptable salt thereof.

10. A pharmaceutical composition comprising a compound of claim 1, or a pharmaceutically acceptable salt thereof, and a therapeutically inert carrier.

11. A compound selected from the group consisting of:

2-fluoroethyl 2-{[6-(cyclopropylmethoxy)-5-(3-methoxyazetidin-1-yl)pyridine-2-carbonyl]amino}-2-ethylbutanoate;

3-fluoropropyl 2-{[6-(cyclopropylmethoxy)-5-(3-methoxyazetidin-1-yl)pyridine-2-carbonyl]amino}-2-ethylbutanoate;

2-fluoroethyl N-[6-(cyclopropylmethoxy)-5-(3-methoxyazetidin-1-yl)pyridine-2-carbonyl]-L-leucinate;

6-(Cyclopropylmethoxy)-N-[(2S)-1-(fluoromethoxy)-4-methylpentan-2-yl]-5-(pyrrolidin-1-yl)pyridine-2-carboxamide;

6-(Cyclopropylmethoxy)-N-[(2S)-1-(2-fluoroethoxy)-4-methylpentan-2-yl]-5-(pyrrolidin-1-yl)pyridine-2-carboxamide; and 6-(Cyclopropylmethoxy)-N-[(2S)-1-(fluoromethoxy)-4-methylpentan-2-yl]-5-(3-methoxyazetidin-1-yl)pyridine-2-carboxamide;

or a pharmaceutical acceptable salt thereof.

12. A compound of claim 11, wherein the compound is 2-fluoroethyl 2-{[6-(cyclopropylmethoxy)-5-(3-methoxyazetidin-1-yl)pyridine-2-carbonyl]amino}-2-ethylbutanoate, or a pharmaceutical acceptable salt thereof.

13. A compound of claim 11, wherein the compound is 3-fluoropropyl 2-{[6-(cyclopropylmethoxy)-5-(3-methoxyazetidin-1-yl)pyridine-2-carbonyl]amino}-2-ethylbutanoate, or a pharmaceutical acceptable salt thereof.

14. A compound of claim 11, wherein the compound is 2-fluoroethyl N-[6-(cyclopropylmethoxy)-5-(3-methoxyazetidin-1-yl)pyridine-2-carbonyl]-L-leucinate, or a pharmaceutical acceptable salt thereof.

15. A compound of claim 11, wherein the compound is 6-(Cyclopropylmethoxy)-N-[(2S)-1-(fluoromethoxy)-4-methylpentan-2-yl]-5-(pyrrolidin-1-yl)pyridine-2-carboxamide, or a pharmaceutical acceptable salt thereof.

16. A compound of claim 11, wherein the compound is 6-(Cyclopropylmethoxy)-N-[(2S)-1-(2-fluoroethoxy)-4-methylpentan-2-yl]-5-(pyrrolidin-1-yl)pyridine-2-carboxamide, or a pharmaceutical acceptable salt thereof.

17. A compound of claim 11, wherein the compound is 6-(Cyclopropylmethoxy)-N-[(2S)-1-(fluoromethoxy)-4-methylpentan-2-yl]-5-(3-methoxyazetidin-1-yl)pyridine-2-carboxamide, or a pharmaceutical acceptable salt thereof.

18. A pharmaceutical composition comprising a compound of claim 11, or a pharmaceutically acceptable salt thereof, and a therapeutically inert carrier.

* * * * *